(12) United States Patent
Kandori et al.

(10) Patent No.: US 8,246,554 B2
(45) Date of Patent: Aug. 21, 2012

(54) LIVING BODY INSPECTION SYSTEM, LIVING BODY INSPECTION APPARATUS, AND LIVING BODY INSPECTION METHOD

(75) Inventors: Akihiko Kandori, Tokyo (JP); Tsuyoshi Miyashita, Fuchu (JP); Yuko Sano, Kokubunji (JP)

(73) Assignee: Hitachi Consumer Electronics Co., Ltd., Tokyo (JP)

( * ) Notice: Subject to any disclaimer, the term of this patent is extended or adjusted under 35 U.S.C. 154(b) by 382 days.

(21) Appl. No.: 12/271,016

(22) Filed: Nov. 14, 2008

(65) Prior Publication Data

US 2009/0118648 A1 May 7, 2009

(30) Foreign Application Priority Data

Nov. 14, 2007 (JP) ................................ 2007-295935
Jun. 19, 2008 (JP) ................................ 2008-161048

(51) Int. Cl.
| | |
|---|---|
| *A61B 5/103* | (2006.01) |
| *A61B 5/117* | (2006.01) |
| *A61B 5/00* | (2006.01) |
| *G01P 15/00* | (2006.01) |
| *G01P 5/00* | (2006.01) |
| *G01P 7/00* | (2006.01) |
| *G01P 9/00* | (2012.01) |
| *G01P 11/00* | (2006.01) |
| *G01L 5/16* | (2006.01) |

(52) U.S. Cl. ........ 600/595; 600/587; 702/141; 702/142; 73/865.3; 73/865.4

(58) Field of Classification Search ................. 600/587, 600/595; 73/865.3, 865.4; 702/94, 104, 702/141, 142, 150, 152, 153
See application file for complete search history.

(56) References Cited

U.S. PATENT DOCUMENTS

| | | | |
|---|---|---|---|
| 2004/0210166 A1* | 10/2004 | Soh et al. ..................... | 600/595 |
| 2005/0065422 A1 | 3/2005 | Kandori et al. | |
| 2006/0244744 A1 | 11/2006 | Kandori et al. | |
| 2007/0038067 A1 | 2/2007 | Kandori et al. | |
| 2007/0038154 A1 | 2/2007 | Kandori et al. | |
| 2007/0272599 A1 | 11/2007 | Miyashita et al. | |

* cited by examiner

*Primary Examiner* — Jeffrey G Hoekstra
*Assistant Examiner* — Devin Henson
(74) *Attorney, Agent, or Firm* — Antonelli, Terry, Stout & Kraus, LLP.

(57) ABSTRACT

Motion of fingers of a subject is dynamically analyzed to provide an estimation index in a hardness of a muscle used in the motion of the fingers. A processing part calculates a speed and acceleration of two fingers on the basis of the motion data of the fingers obtained by a tapping detecting unit, calculates a ratio between the speed and the acceleration, and calculates as an estimation index a mechanical impedance regarding extending force of the fingers and a mechanical impedance regarding opening and closing force of the fingers by applying the calculated ratio to a predetermined equation based on a muscle dynamic model.

14 Claims, 17 Drawing Sheets

FIG.9A  PRIOR ART
GENERAL HILL MODEL
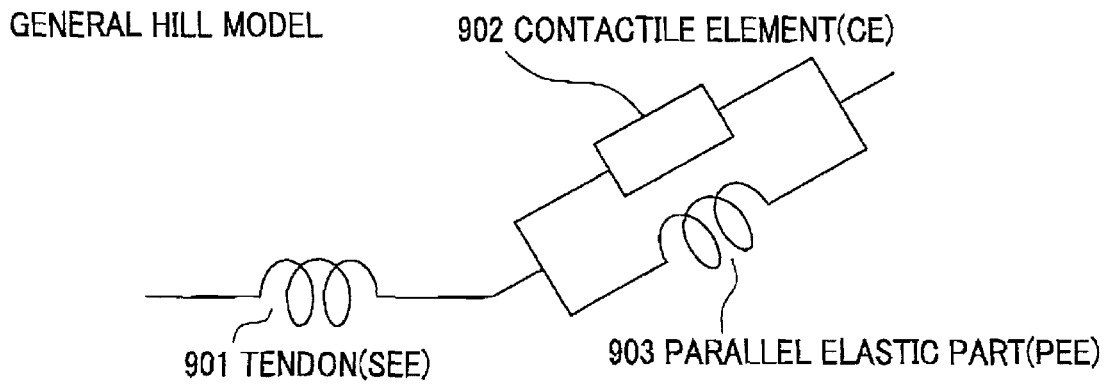
901 TENDON(SEE)
902 CONTACTILE ELEMENT(CE)
903 PARALLEL ELASTIC PART(PEE)
FIG.9B  THIS INVENTION
TAPPING MODEL ACCORDING TO HILL MODEL
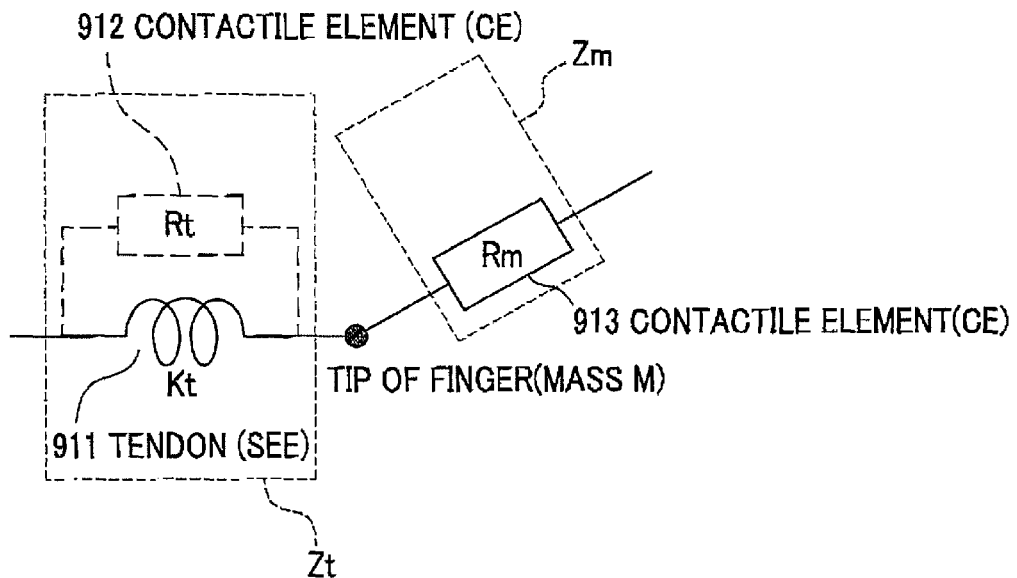
912 CONTACTILE ELEMENT (CE)
913 CONTACTILE ELEMENT(CE)
911 TENDON (SEE)
TIP OF FINGER(MASS M)

FIG.10A AGED PEOPLE
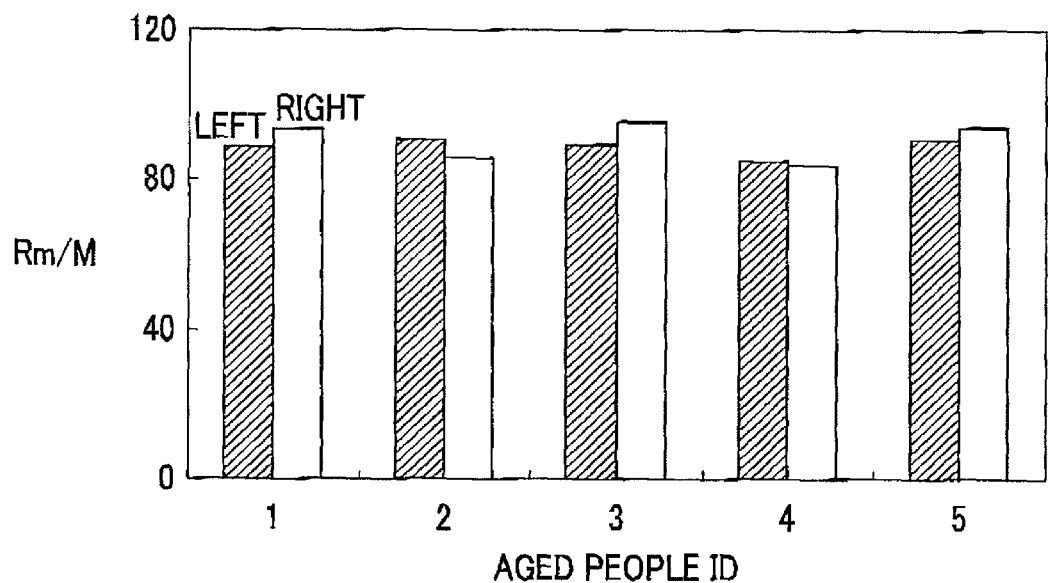
FIG.10B
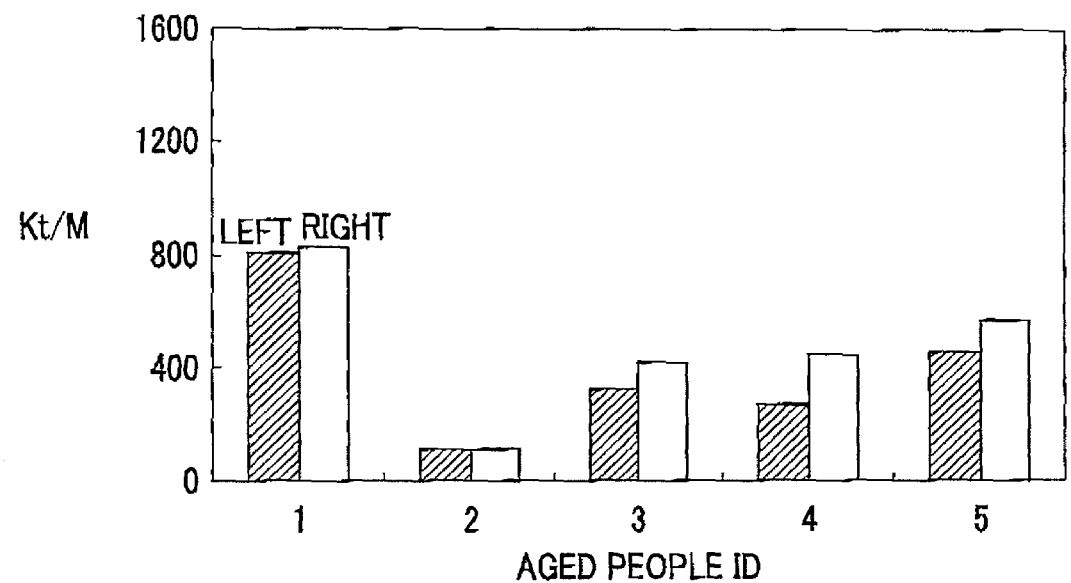

PARKINSON'S DISEASE

IN NEARLY OPEN CONDITION OF FINGER
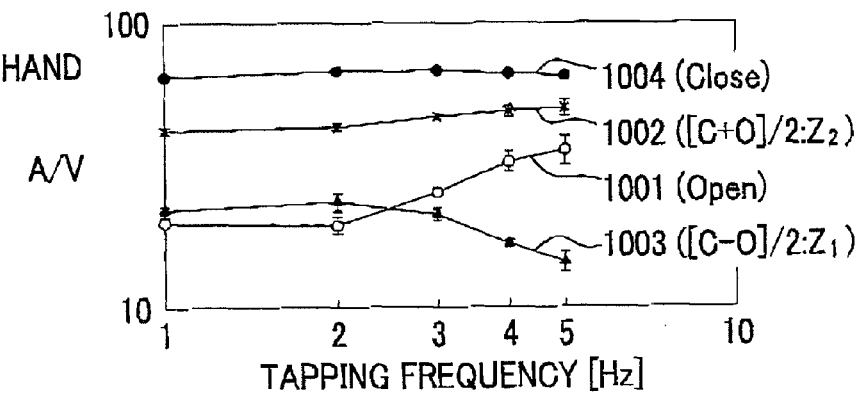
FIG.15A WOMAN, LEFT HAND
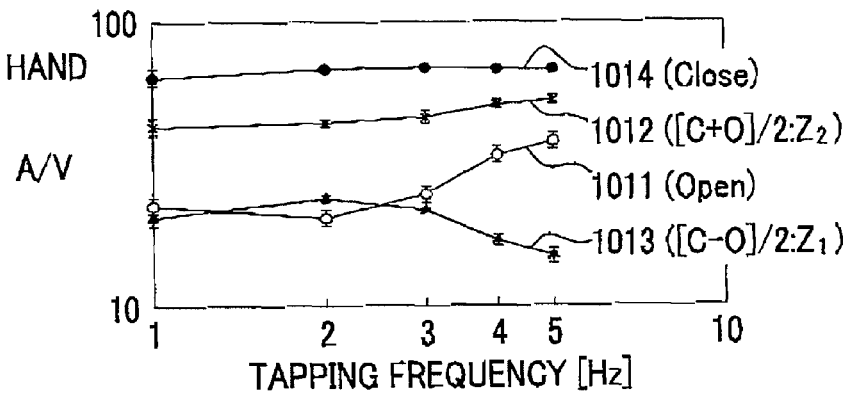
FIG.15B WOMAN, RIGHT HAND
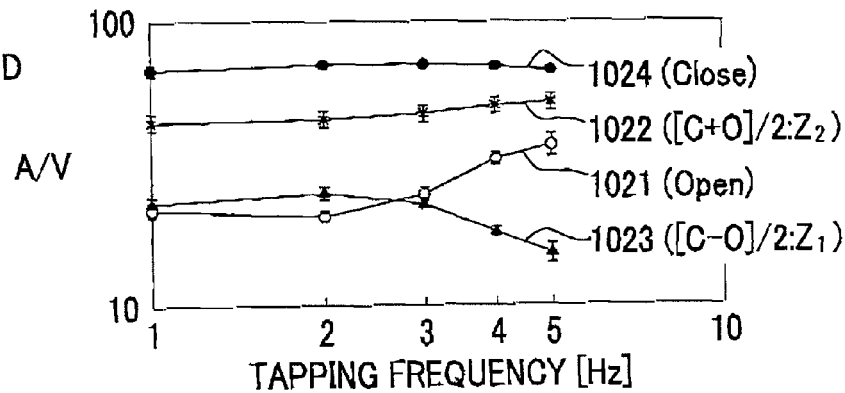
FIG.15C MAN, LEFT HAND
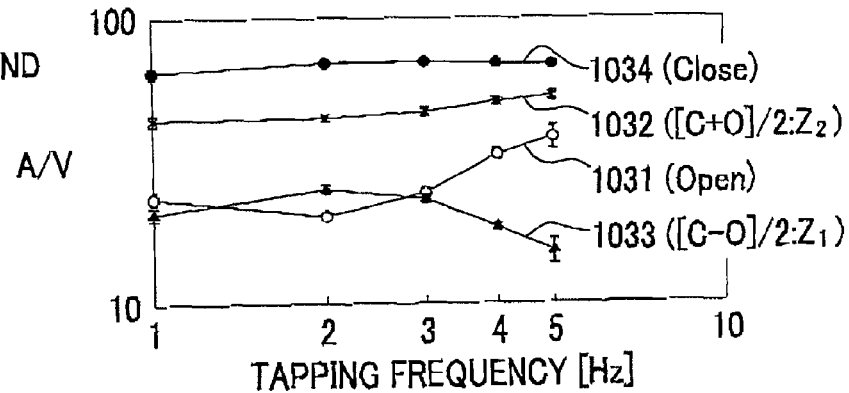
FIG.15D MAN, RIGHT HAND FIG. 16
IN NEARLY CONTACT CONDITION OF FINGER
FIG.16A
WOMAN, LEFT HAND
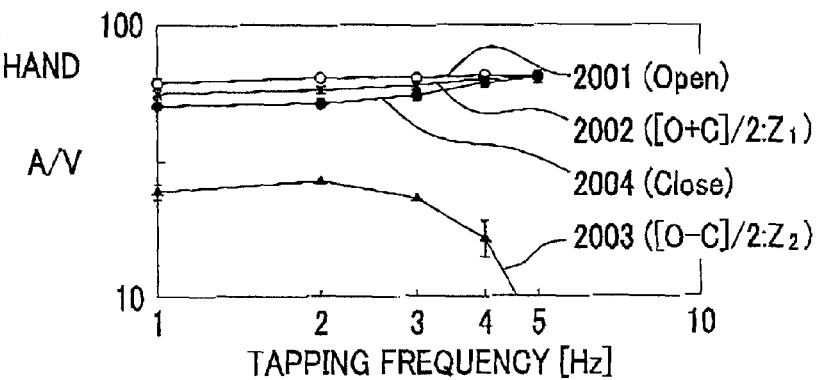
FIG.16B
WOMAN, RIGHT HAND
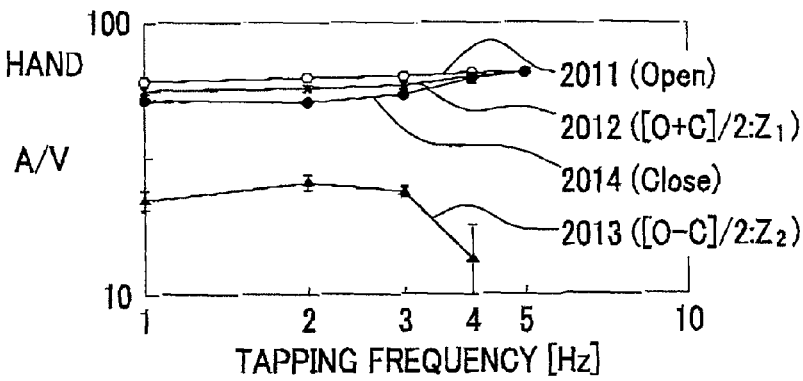
FIG.16C
MAN, LEFT HAND
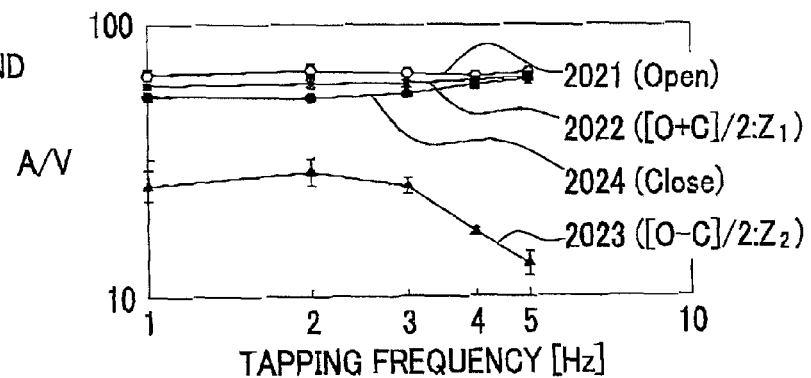
FIG.16D
MAN, RIGHT HAND
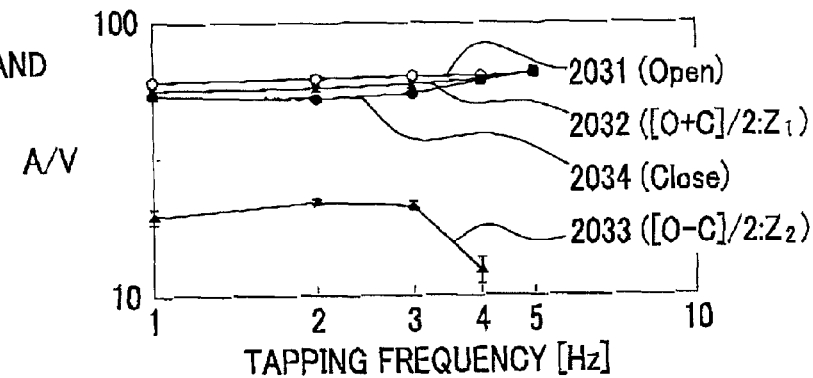

IN NEARLY OPEN CONDITION OF FINGERS

IN NEARLY CONTACT CONDITION OF FINGERS

FIG.18A  IN NEARLY OPEN CONDITION
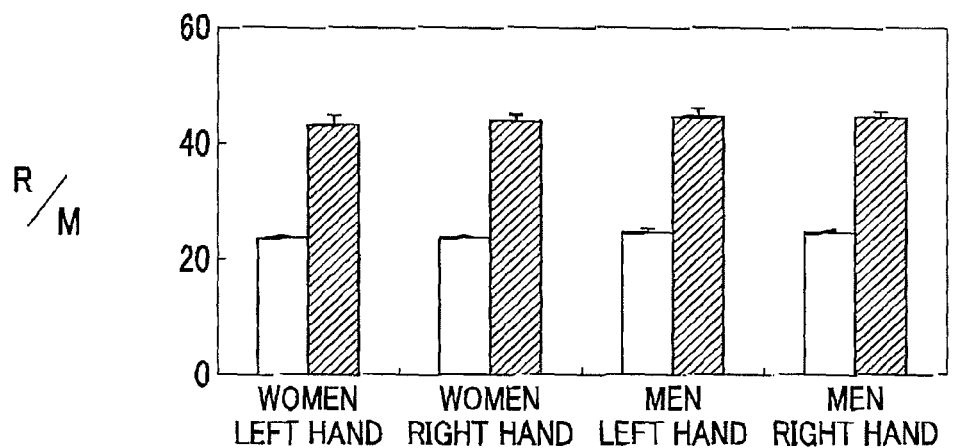
FIG.18B
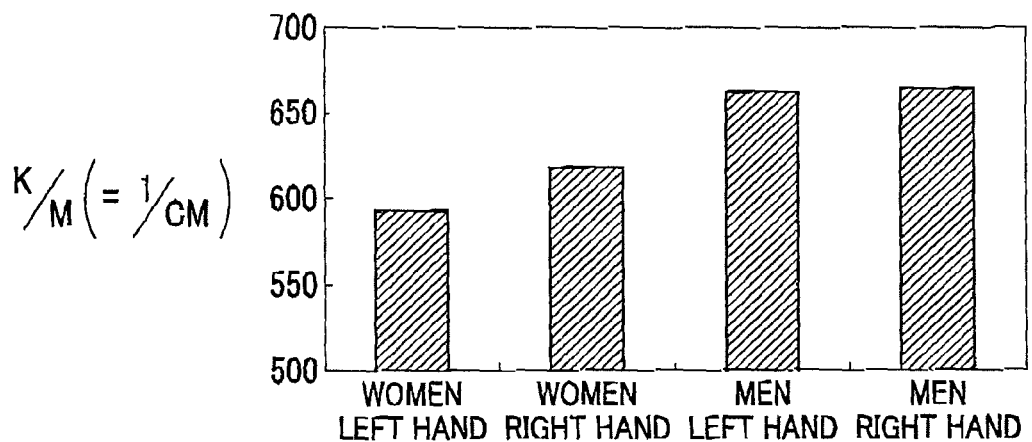
FIG.18C  IN NEARLY CONTACT CONDITION
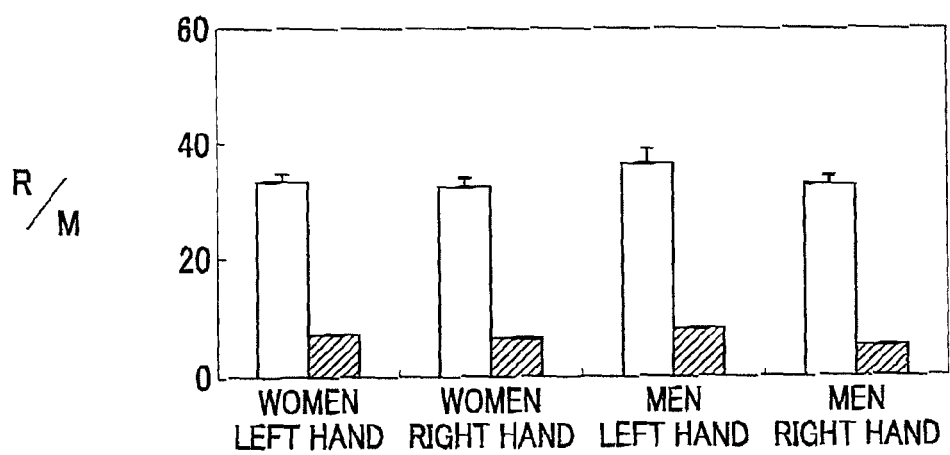

LIVING BODY INSPECTION SYSTEM, LIVING BODY INSPECTION APPARATUS, AND LIVING BODY INSPECTION METHOD

CROSS REFERENCE TO RELATED APPLICATIONS

This application claims the foreign priority benefit under Title 35, United States Code, §119(a)-(d) of Japanese Patent Application No. 2007-295935, filed on Nov. 14, 2007 and Japanese Patent Application No. 2008-161048, filed on Jun. 19, 2008 in Japan Patent Office, the disclosure of which is herein incorporated by reference in its entirety.

BACKGROUND OF THE INVENTION

1. Field of the Invention

The present invention relates to a living body inspection system, a living body inspection apparatus, and a living body inspection method.

2. Description of the Related Art

A living body inspection apparatus capable of detecting motion of parts of a living is known which monitors motion of fingers or the like to estimate decrease in motion or rhythm disturbance due to a brain disease such as Parkinson's disease. US Patent Application Publication No. 2005/0065422A1 discloses a living body inspection apparatus capable of detecting the motion of parts of a living body with use of a coil generating a magnetic field (see US Patent Application Publication 2005/0065422A1, FIG. 1).

SUMMARY OF THE INVENTION

A first aspect of the present invention provides a living body inspection system comprising: a tapping detecting unit for detecting motion data regarding at least one of a distance, a speed, and an acceleration, of two fingers of a hand of a subject, in tapping operation including open and closing motions of the fingers; and a living body inspection apparatus for calculating an estimation index regarding finger motion of the subject on the basis of the motion data. The living body inspection apparatus comprises: a storage; and a processing part for obtaining the speed and the acceleration on the basis of the motion data from the tapping detection unit, calculating the estimation index by calculating at least one of an index regarding extending force of fingers and an index regarding open and closing force of the fingers to store the estimation index in the storage.

A second aspect of the present invention provides a living body inspection method of calculating an estimation index regarding finger motion of the subject on the basis of motion data obtained from a tapping detecting unit for detecting the motion data regarding at least one of a distance, a speed, and an acceleration, of two fingers of a hand of a subject, in open and closing motion of the fingers with a living body inspection apparatus comprising a storage and a processing part, comprising the steps of: in the processing part, obtaining the speed and the acceleration on the basis of the motion data from the tapping detection unit; and calculating the estimation index by calculating at least one of an index regarding extending force of fingers and an index regarding open and closing force of the fingers to store the estimation index in the storage.

BRIEF DESCRIPTION OF THE DRAWINGS

The object and features of the present invention will become more readily apparent from the following detailed description taken in conjunction with the accompanying drawings in which:

FIG. 9A is an illustration of a prior art muscle model called Hill model;

FIG. 9B is in illustration of a model according to the first embodiment;

FIGS. 10A and 10B are charts of experimental data using five aged-peoples who are healthy without histories of brain disease according to the first embodiment;

FIGS. 15A to 15D are charts for showing analysis results of finger motions measured by the periodic test regarding motion of two fingers in the nearly open condition according to the second embodiment;

FIGS. 16A to 16D show analysis results of finger motions measured by the periodic test regarding motion of two fingers in the nearly contact condition according to the second embodiment;

FIGS. 18A and 18B show data regarding motions of two fingers in the nearly open condition according to the second embodiment; and FIG. 18C shows data regarding motions of two fingers in the nearly contact condition according to the second embodiment.

DETAILED DESCRIPTION OF THE INVENTION

Prior to describing an embodiment of the present invention, the above-mentioned related art will be further explained.

US Patent Application Publication No. 2005/0065422A1 does not dynamically analyze motion of fingers of the subject and does not obtain an estimation index in hardness, etc, of a muscle used in the motion of the fingers of the subject. The present invention provides an appropriate estimation index in hardness, etc. of a muscle used in the motion of the fingers of the subject through dynamically analyzing the motion of the fingers of the subject.

With reference to drawings will be described embodiments of the present invention.

First Embodiment

Structure

Figure 1:
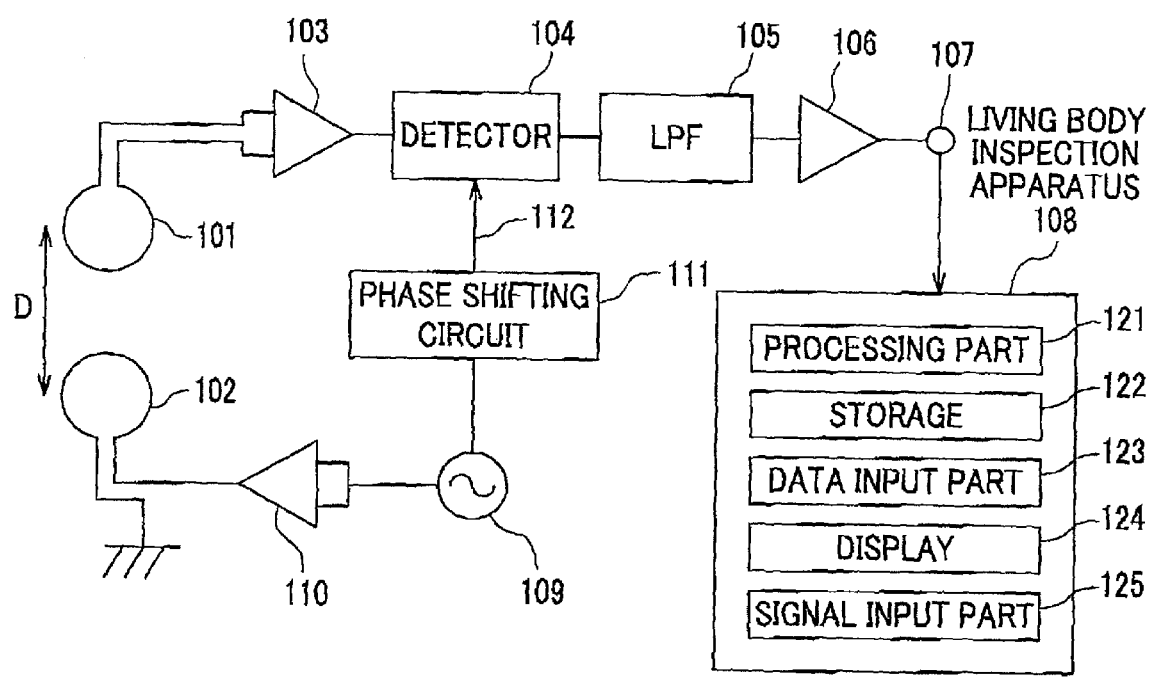
FIG. 1 is a block diagram of a living body inspection apparatus according to first and second embodiments of the present invention.

FIG. 1 is a block diagram of a living body inspection apparatus according to first and second embodiments of the present invention.

An AC voltage generating circuit 109 generates an AC voltage having a specific frequency (for example 20 kHz). The AC voltage having the specific frequency generated by the AC voltage generating circuit 109 is converted into an alternating current having the specific frequency by a current generating amplifier 110. The alternating current converted by the alternating current generating amplifier 110 is supplied to a oscillation coil 102. A magnetic field generated from the current flowing through the oscillation coil 102 generates an induced voltage in a detection coil 101. For example, the oscillation coil 102 is attached to either of the hands of a subject, and the detection coil 101 is attached to an index finger of the same hand of the subject. This will be more specifically with reference to FIGS. 1 and 2.

The induced voltage generated in the detection coil 101 (having the same frequency as the AC voltage generated by the AC voltage generating circuit 109) is amplified by a preamplifier 103 and the amplified signal is supplied to a detector 104. The detector 104 conducts detection with the specific frequency generated by the AC voltage generating circuit 109 or a double frequency of the specific frequency. For this, a phase shifting circuit 111 adjusts a phase of an output of the AC voltage generating circuit 109 to generate a reference signal 112 which is applied to a reference signal input terminal of the detector 104 for detection the reference signal 112.

If the detection is conducted at the double frequency, the phase shifting circuit 111 is not necessarily required. A simple circuit configuration for detecting at twice the specific frequency is one where the specific frequency of the alternating current generating circuit 109 is set at the frequency twice the original specific frequency and divided into half the specific frequency, which is input to the current generating amplifier 110. A signal having a frequency twice the specific frequency of the AC voltage generating circuit 109 may be input as the reference signal 112 to the reference signal input terminal of the detector 104.

The output signal of the detector 104 passes through an LPF (Low-Pass Filter) circuit 105 and is amplified by an amplifier 106 to generate an output signal 107 with a desired voltage and is applied to the living body inspection apparatus 108. The output signal 107 has a voltage corresponding to a distance D between the oscillation coil 102 and the detection coil 101 attached to the thumb and the index finger, respectively. These elements are included in a tapping device except the output signal 107 and the reference signal 112.

The living body inspection apparatus 108 comprises a computer for recording and analyzing the output signal 107 and includes a processing part, a storage 122, a data input part 123, a display 124, and a signal input part 125.

The processing part 121 analyzes motion of fingers of a subject dynamically on the basis of the output signal 107 to display the analysis results on the display 124 using a CPU (Central Processing Unit).

The storage 122 comprises a storing apparatus or a temporarily storing device for storing various programs, data, and the analysis results, and the like. For example, the storage comprises a ROM (Read Only Memory), a RAM (Random Access Memory), a hard disk drive, or the like. The processing part 121 can conduct various operations through installing programs in the storage 122 and data and the like in the storage 122 and can store the data and the analysis results in the storage 122.

The data input part 123 is provided to input data regarding a subject by an operator of the living body inspection apparatus 108, and for example, comprises a keyboard, a mouse, and the like. The data input part 123 may have a function of GUI (Graphical User Interface).

The display 124 is provided to display the data and the analysis results generated by the processing part 121 and, for example, comprises an LCD (Liquid Crystal Display), a CRT (Cathode Ray Tube), or the like.

The signal input part 125 is an interface circuit for detection the output signal 107 from the amplifier 106.

Figure 2:
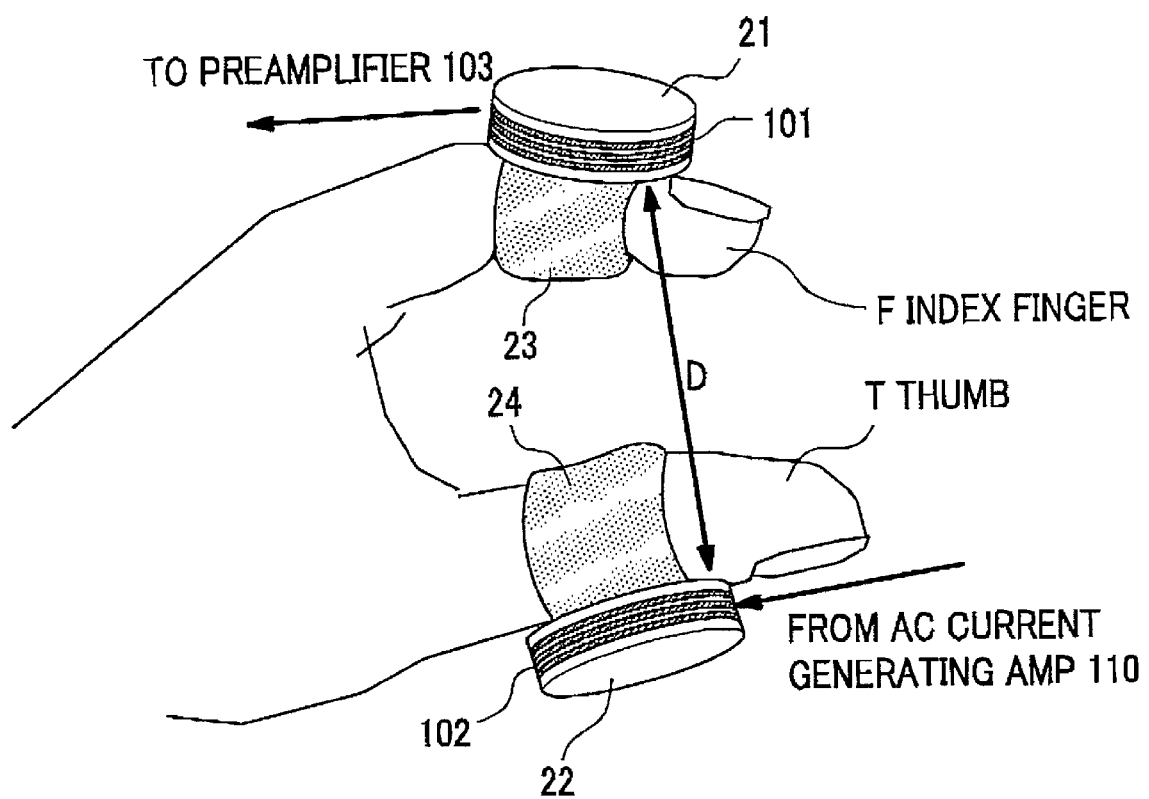
FIG. 2 is an illustration for showing a hand to which transmitting and detection coils are attached according to first and second embodiments.

FIG. 2 is an illustration for showing a condition where the oscillation coil 102 and the detection coil 101 are attached to a hand (left hand in FIG. 2) of a subject.

As shown in FIG. 2, the oscillation coil 102 which is connected to the current generating amplifier 110 and is provided by winding a wire around a coil bobbin 22 which is fixed to a band 24 which is attached to the thumb T, so that the coil bobbin 22 and the oscillation coil 102 are fixed to the thumb T.

Similarly, the detection coil 101 which is connected to the preamplifier 103 and is provided by winding a wire around a coil bobbin 21 which is fixed to a band 23 which is attached to the index finger F, so that the coil bobbin 21 and the detection coil 101 are fixed to the index finger F.

The bands 23 and 24 are made of a rubber or sponge to absorb difference in thickness of fingers among subjects.

Using this structure, the distance D can be determined from the voltage of the output signal 107 on the basis of a relation between the voltage of the output signal 107 and the distance D between the thumb T and the index finger F previously stored in the storage 122 of the living body inspection apparatus 108. The fingers to be fixed to the oscillation coil 102 and the detection coil 101 are not limited to the thumb T and the index finger F, but may be other fingers.

Figure 3A:
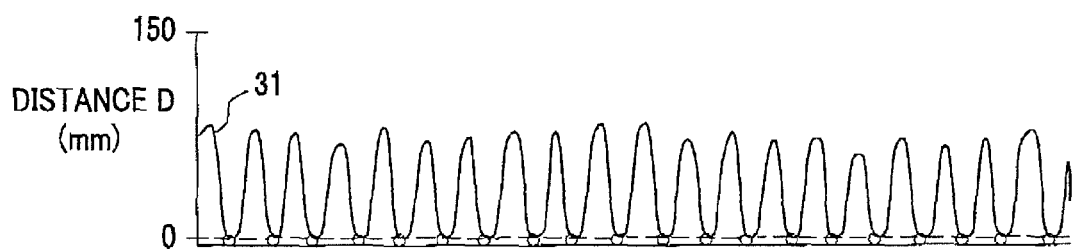
FIGS. 3A to 3C are charts for showing an example of data obtained from tapping (open-close operation by the thumb and another finger) by a subject.
Figure 3B:
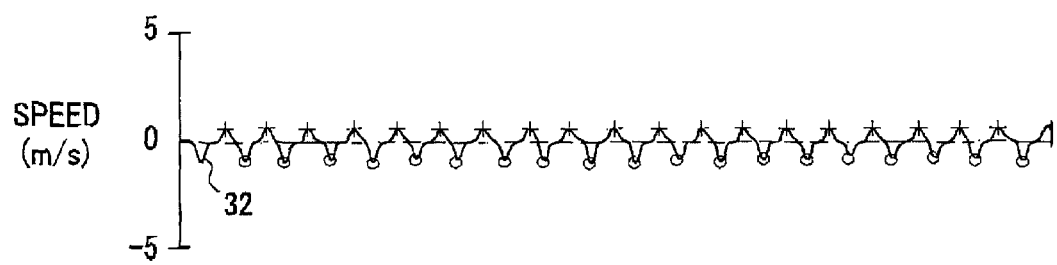
Figure 3C:
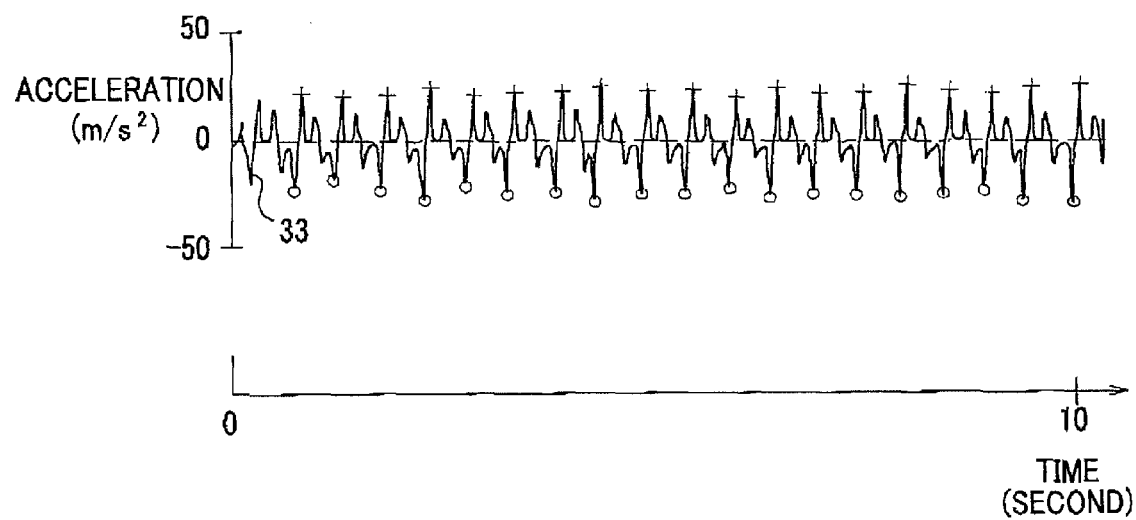

FIGS. 3A to 3C are charts for showing an example of data obtained from tapping (open-close operation by the thumb and another finger) by the subject. FIG. 3A shows a relation between a distance D between two fingers (thumb T and the index finger F) and time, FIG. 3B shows a relation between time and a relative speed (speed) between two fingers. FIG. 3C shows a relation between time and a relative acceleration (acceleration) between two figures.

In the following description, both "local maximum value" and "local minimum value" are referred to as "local maximum value". In other words "local minimum value" is not used throughout the specification. In other words, both a maximum and a minimum value at a predetermined section of sequentially obtained data of a function are referred to as "local maximum value".

As shown in FIG. 3A, a waveform (distance waveform) 31 represents time variation in the distance D between two fingers, wherein parts denoted with open circles (o) (valleys of the waveform) represents that the distance D is zero, i.e., timing when two fingers contact. The waveform 31 is generated by that the processing part 121 of the living body inspection apparatus 108 converts voltage values of the output signal 107 into a distance.

As shown in FIG. 3B, a waveform 32 (speed waveform) represents a time variation in the relative speed (m/s) between two fingers. Parts denoted with crosses (+) represent positive peaks (local maximum values) in speed while two fingers are opened. Parts denoted with the open circles (o) represent negative peaks (local maximum values) in the speed while two fingers are closed. In other words, in the speed, a direction in opening is defined as a positive direction. Similarly, in the acceleration, a direction in opening is defined as a positive direction. The processing part 121 of the living body inspection apparatus 108 generates a waveform 32 by time-differentiating the waveform 31 representing the distance D between two fingers. In the waveform 32, the speed is 0 m/s when two fingers contact. Similarly, timing is also 0 m/s when two fingers are fully opened.

As shown in FIG. 3C, a waveform 33 (acceleration waveform) represents the relative speed between two fingers. Parts denoted with crosses (+) in FIG. 3C represent positive peaks of the acceleration in opening. Parts denoted with open circles (o) represent negative peaks in the acceleration while two fingers are being closed. The processing part 121 of the living body inspection apparatus 108 generates a waveform 33 by time-differentiates the waveform 32.

Hereinafter, the distance waveform, the speed waveform, and the acceleration waveform are referred to as "motion waveforms". Here, even in a case where a strain gage, an accelerometer, or the like is used in place of the oscillation coil 102 and the detection coil 101, where at least one of motion waveforms is measured, other motion waveforms can be complementarily obtained by differential and integrating calculation. Generating the motion waveforms are disclosed in US Patent Application Publication 2005/0065422A1, the disclosure of which is herein incorporated by reference in its entirety. Thus, a duplicated description will be omitted.

Next, will be described a kinematics analysis model according to this embodiment. In the blow description, a mechanical impedance is a quantity representing uneasiness in motion of an object (finger) and is determined on the basis of a mass of the object, a mechanical resistance (friction or the like) when the object moves, and a spring constant in which a tendon corresponds to a spring. The mechanical impedance is so named because it corresponds to impedance in an electric circuit.

Two Eqs. (1) and (2) below are considered which use kinematics equations in consideration of the mechanical impedance and a law of inertia.

$$F = ZV \quad (1)$$

$$F = MA \quad (2)$$

Here, F (N=kg·m/s$^2$) is defined as a force applied to a finger, Z(kg/s) is a mechanical impedance of the finger, M (kg) represents a mass of the fingers. "A" (m/s$^2$) represents an acceleration of the finger, and V (m/s) represents a speed of the finger.

Solving simultaneous equations, i.e., Eqs. (1) and (2), provides the following Eq. (3).

$$\frac{Z}{M} = \frac{A}{V} \quad (3)$$

As shown in Eq. (3), it is known that a mechanical impedance (Z/M) which is a mechanical impedance normalized by the mass of the finger can be estimated with a value of A/V. It is considered that the normalizing can absorb difference among subjects in size of fingers. In the first embodiment, a model analysis is carried out with the value of A/V. In other words, obtaining the value of A/V indirectly obtains a value of Z/M. This provides the value of Z/M without directly measuring or directly calculating the mechanical impedance and the mass (M) of the finger.

To estimate the value of A/V, local maximum values of the speed and the acceleration in opening periods of tapping (hereinafter referred to as local maximum speed and local maximum acceleration), and local maximum speeds and local maximum speeds in closing periods of tapping are extracted from the waveforms in FIGS. 3B and 3C at all tapping cycles. Average values of the local maximum speeds and the local maximum accelerations extracted are calculated. It is assumed that an average local maximum speed in the opening periods is Vo, an average local maximum acceleration in the opening periods is Ao, an average local maximum speed in the closing periods is Vc, and an average local maximum acceleration in the closing periods is Ac.

Will be described an example of a measuring method and an analysis result thereof.

When motions of fingers are measured, the subject wears the oscillation coil 102 on the thumb T and the detection coil 101 on the index finger F, and conducts tapping in this condition. The distance between both coils is measured.

Here, instead the bands 23 and 24, the oscillation coil 102 may be attached to a nail of the thumb T and the detection coil 101 may be attached to a nail of the index finger F with a medical double-sided adhesive tape or the like. Further, arrangement of the oscillation coil 102 and the detection coil 101 is not dependent on which one is on the thumb T or on the index finger F, and the attachment places are not limited to the nails.

Next, a magnetic field of 20 kHz is generated by the oscillation coil 102 and a voltage induced in the detection coil 101 is detected. Next, the detected induced voltage is subjected to rock-in detection (only components having frequency around 20 kHz are detected). The distance between the fingers is measured by converting the output of the rock-in detection into distance. These operations are the same as those described with reference to FIG. 1.

The subject conducts tapping in a relaxed sitting position. There are two kinds of testing, namely, a periodical test with tapping timed to timing of 1, 2, 3, 4, and 5 Hz using a metronome, and a non-periodical test with tapping as fast and largely in opening as possible (frequency is approximately from 2 to 5 Hz).

Figure 4A:
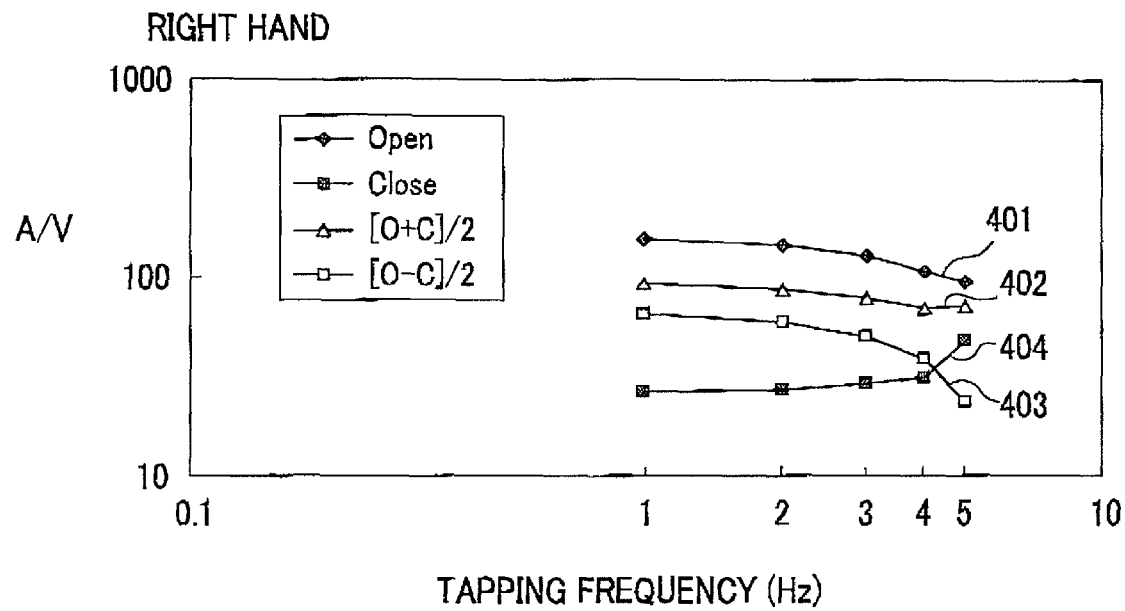
FIGS. 4A and 4B are charts for showing analysis results of motion of fingers measured by the periodic test.
Figure 4B:
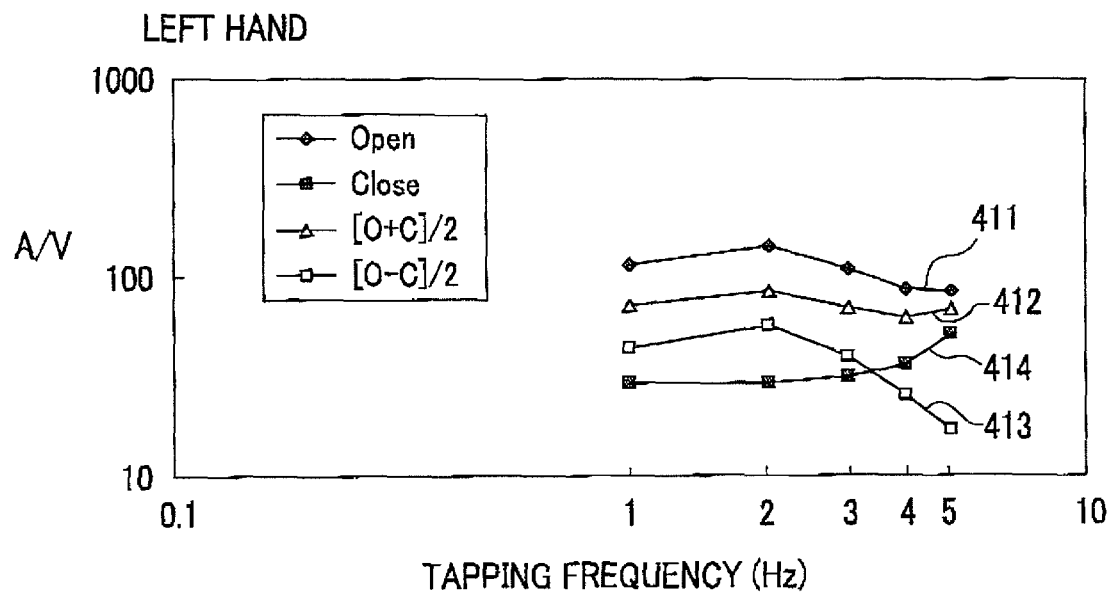

FIGS. 4A and 4B show the analysis results of the motion of fingers measured by the periodic test (average among three subjects).

FIG. 4A shows the analysis result of the right hand, and FIG. 4B shows the analysis result of the left hand. As shown in FIGS. 4A and 4B, in the analysis results of both right (which is dominant hand for all three subjects) and left hands, the values of A/V (denoted with "401" and "411") are relatively large at all frequencies in the opening period. Further, there are tendencies that as the frequency increases, the values of A/V (denoted with "404" and "414") become large in the closing period and on the other hand, the values of A/V (denoted with "401" and "411") becomes small in the opening period.

These tendencies show that a value which is obtained by adding the values of A/V in the closing and opening periods, is divided by two [(O+C)/2] (denoted with references "402" and "412") is not largely dependent on the frequency, but is a constant value. On the other hand, it is known that a value obtained by subtracting the value of A/V in the closing period from that in the opening period [(O−C)/2] (denoted with references "403" and "413") becomes low with increase in the frequency. These tendencies are found in both hands.

Muscle Dynamic Model of Tapping (Analysis Model)

With reference to the relation between the value of A/V and the frequency shown in FIG. 4 will be described a muscle dynamic model.

First, it is assumed that a tip of the finger has a mass M, and is opened and closed at the speed V and the acceleration A. Further, motion of the mass M is determined by a balance between a mechanical impedance Zt influencing on an extending force Ft and a mechanical impedance Zm influencing on opening and closing forces (Fm). Here, the extending force Ft is considered as force always pushing the mass M toward the tip of the finger in a direction of closing (approaching each other). In such a model, it is considered that the mechanical impedance Zt is determined on the basis mainly of an extender tendon (a tendon of finger) and the mechanical impedance Zm is determined on the basis mainly of a flextor muscle (a muscle of finger).

Figure 5:
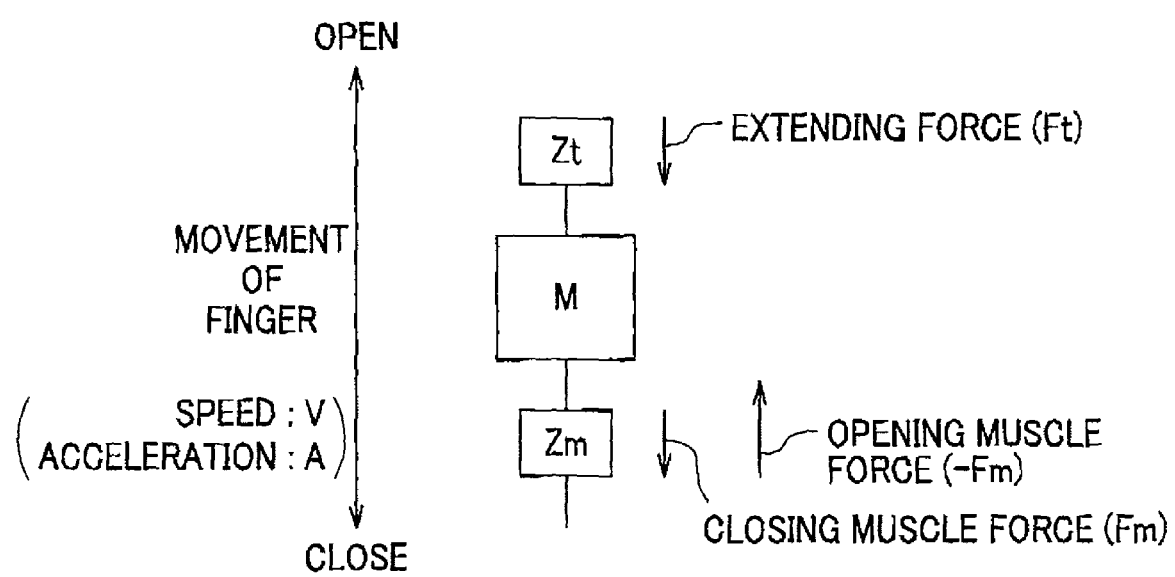
FIG. 5 is a schematic illustration of a muscle dynamic model according to the first embodiment.

FIG. 5 schematically shows this the muscle dynamic model. In FIG. 5, because it is considered that the extending force Ft always pushes the mass M of the finger tip in a closing direction of the finger, a muscle force (−Fm) opening the finger having a magnitude greater than a muscle force (Fm) closing the finger is necessary.

When the finger moves in the opening direction, the following Eq. (4a) is established and can be converted into Eq. (4b) through modification with Eq. (1), and Eq. (4c) can be given by further modification.

$$-F_m + F_t = -MA_o \quad (4a)$$

$$(Z_m - Z_t)V_o = MA_o \quad (4b)$$

$$\frac{(Z_m - Z_t)}{M} = \frac{A_o}{V_o} \quad (4c)$$

Further, when the fingers move in the closing direction, the following Eq. (5a) is established and can be converted into Eq. (5b) through modification with Eq. (1), and Eq. (5c) can be given by further modification.

$$F_m + F_t = MA_c \quad (5a)$$

$$(Z_m + Z_t)V_c = MA_c \quad (5b)$$

$$\frac{(Z_m + Z_t)}{M} = \frac{A_c}{V_c}. \quad (5c)$$

Solving simultaneous equations, i.e., Eq. (4c) and (5c), provides the following Eq. (6) (a predetermined calculation equation) and Eq. (7) (a predetermined calculation equation).

$$\frac{Z_m}{M} = \left(\frac{A_o}{V_o} + \frac{A_c}{V_c}\right)/2 \quad (6)$$

$$\frac{Z_t}{M} = \left(\frac{A_o}{V_o} - \frac{A_c}{V_c}\right)/2 \quad (7)$$

Using Eqs. (6) and (7) the values of Zm/M and Zt/M can be obtained (estimated from the values of Ao, Ac, and Vo).

Figure 6:
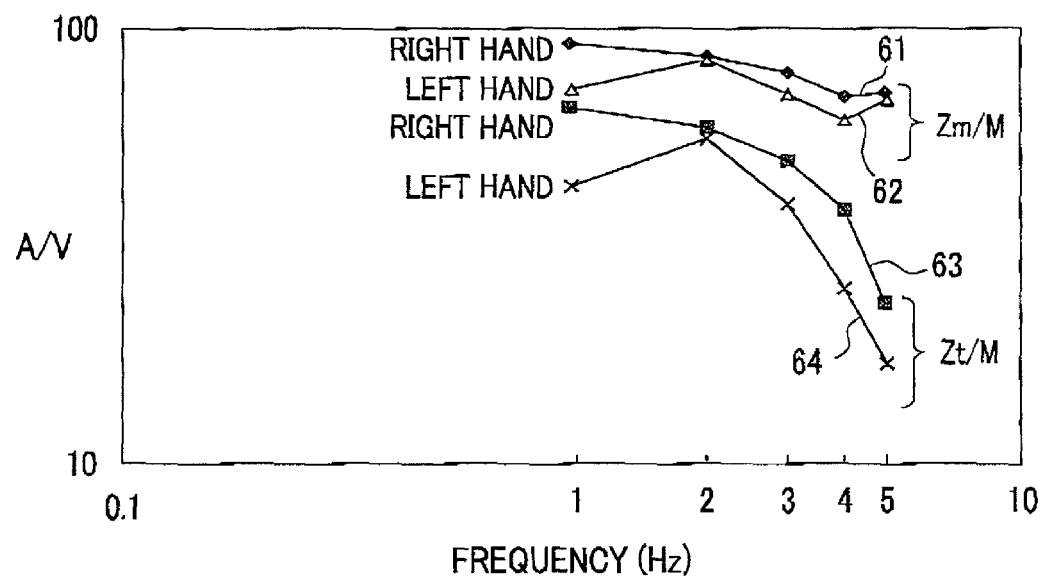
FIG. 6 is a chart of Zm/M and Zt/M per frequency according to the first embodiment.

Calculating the values of Zm/M and Zt/M with eqs. (6) and (7) provides results shown in FIG. 6. FIG. 6 shows the values of Zm/M and Zt/M per frequency.

FIG. 6 shows that Zm/M (denoted with references 61 and 62) has low frequency dependency, and thus is nearly a constant value. On the other hand, FIG. 6 shows that Zt/M (denoted with references 63 and 64) rapidly decreases with increase in frequency.

Figure 7A:
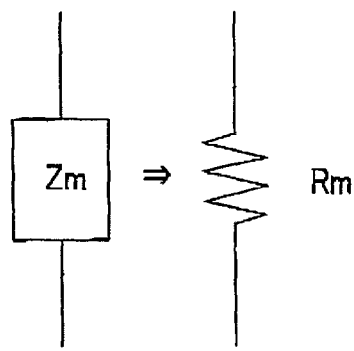
FIGS. 7A to 7C show equivalent circuits for Zm, and an equivalent circuit for Zt according to the first embodiment.
Figure 7B:
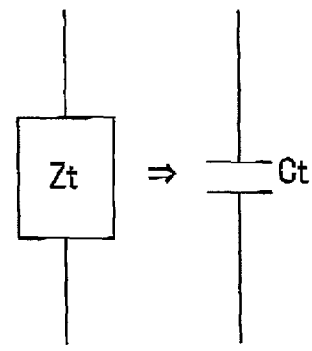
Figure 7C:
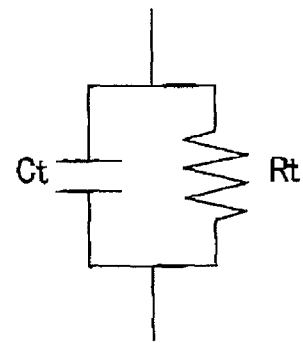

From the calculation result shown in FIG. 6, it is considered that for Zm a mechanical resistance (Rm) is mainly dominant, and Zt mainly reflects a frequency characteristic due to compliance (Ct: an elasticity or strength in flexibility on application of an external force (1/Ct is a spring constant Kt of the tendon). This analysis provides equivalent circuits for Zm and Zt as shown in FIGS. 7A to 7C. If each parameter is normalized with the mass as below, dividing each parameter with M provides normalized one.

FIG. 7A shows an equivalent circuit for Zm. An equivalent circuit for Zt is shown in FIG. 7B or 7C. In FIG. 7B, because Zt has a characteristic of which magnitude decreases with increase in frequency and a characteristic where a portion from 1 Hz to 2 Hz is relatively flat, an equivalent circuit including Ct and Rt connected in parallel can be also considered. Thus, a model having the parallel connection is also considered.

As shown in FIG. 7A, Zm is given by Eq. (8).

$$Z_m = R_m \quad (8)$$

Further, Zt is approximated only with Ct as shown in FIG. 7B. Then, Zt is given by Eq. (9), and a magnitude of Zt is given by Eq. (10). In these equations, "j" indicates an imaginary unit, and "ω" indicates an angular frequency.

$$Z_t = \frac{1}{j\omega C_t} \quad (9)$$

$$|Z_t| = \left|\frac{1}{\omega C_t}\right| \quad (10)$$

When Zt is approximated with a parallel connection of Ct and Rt as shown in FIG. 7C, Zt is calculated in admittance (Yt=1/Zt) which is an inverse number of Zt. Then, Yt and the magnitude are given by Eqs. (11) and (12).

$$Y_t = \frac{1}{R_t} + j\omega C_t \quad (11)$$

$$|Y_t| = \sqrt{\frac{1}{R_t^2} + \omega^2 C_t^2} \quad (12)$$

Figure 8A:
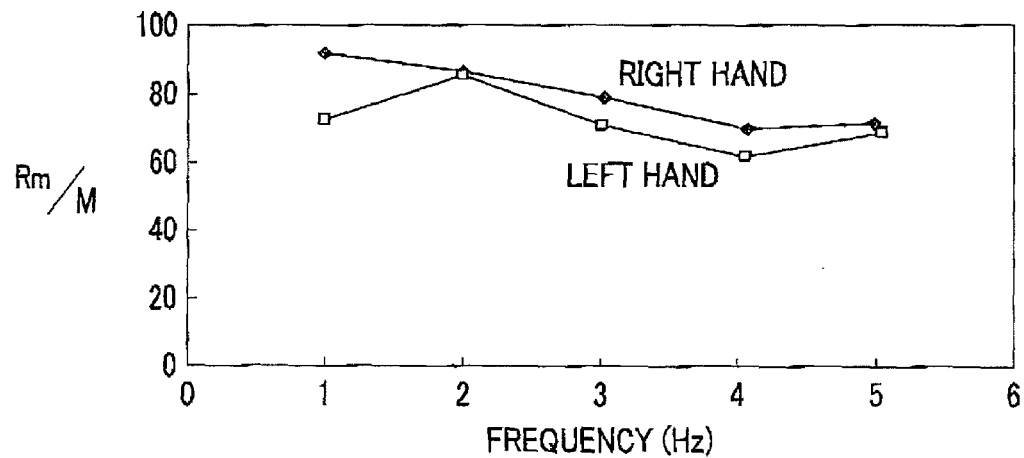
FIG. 8A is a chart of Rm/M according to the first embodiment.
Figure 8B:
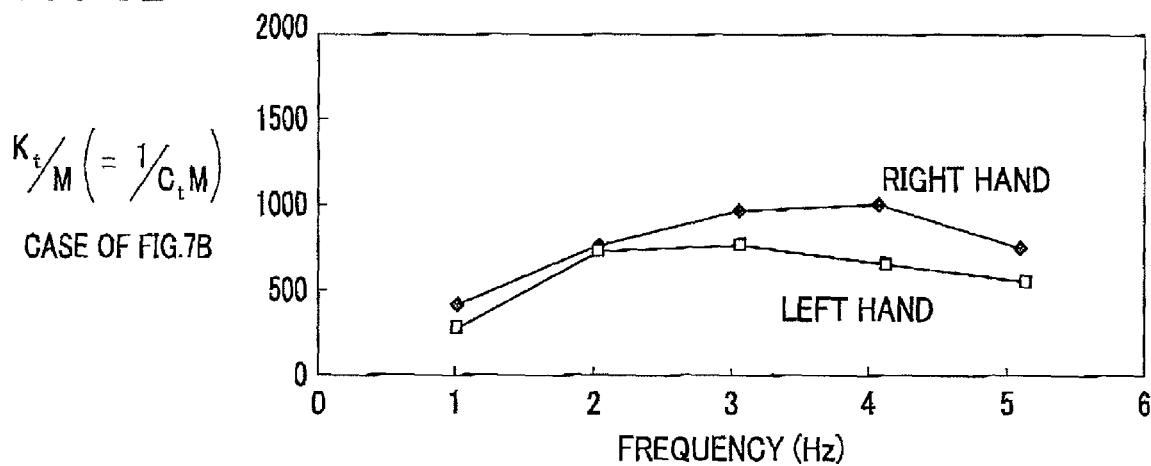
FIGS. 8B and 8C are charts of Kt/M (−1/CtM) according to the first embodiment.
Figure 8C:
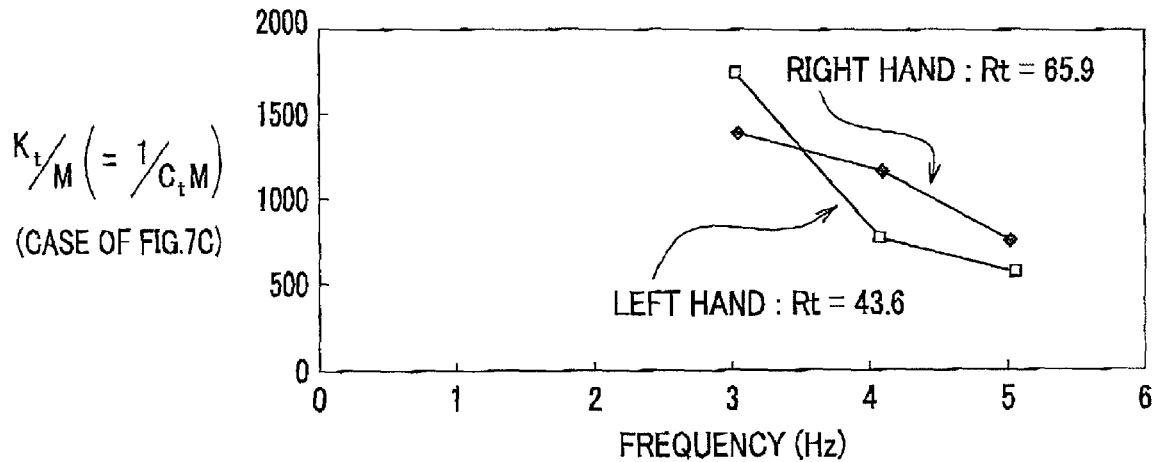

FIGS. 8A to 8C show Rm/M and Kt/M (=1/CtM) obtained by calculation and normalizing by Eqs. (8), (10), and (12). As shown in FIG. 8A, although there is a slight tendency that Rm/M decreases at both right and left hands, but Rm/M is nearly a constant and lies approximately from 70 to 80.

Kt/M which is calculated only with Ct in a case shown in FIG. 7B is equal to or smaller than 400 around 1 Hz where the characteristic is nearly flat. However, after 2 Hz, the value ranges from 500 to 1000, which shows that a relatively stable value can be obtained as shown in FIG. 8B.

On the other hand, the calculation in the parallel connection as shown in FIG. 7C, "1/CtM" is calculated with assumption that a value of Zt/M at 1 Hz where the characteristic curve is flat is equal to a value of Rt/M as it is. The value of 1/CtM has such a tendency as to decrease with increase in frequency as shown in FIG. 8C.

Here, as mentioned above, simplified calculations are made. As another method of calculating values of Rt and Ct, the values can be calculated from values measured at two points, for example, at 1 and 3 Hz. The inventors tried calculation adaptively to actual data However, the inventor could not obtain a solution because of mismatching between the model and the actual values. From these results, it is most appropriate to approximate Zt only with Ct at frequencies of 2 Hz or more.

To consider a muscle dynamic model of tapping, it is most adequate that the mechanical impedance Zm in extending forces of two fingers is mainly caused by, or assumed as the mechanical resistance Rin, in the muscles for opening and closing fingers such as the flextor muscle. Further, it is most adequate that the mechanical impedance Zt of open-close force by two fingers is mainly caused by, or assumed as the compliance Cm(1/K) which serves as a role of a spring such as the extender tendon.

These estimation results show a possibility in that in healthy persons, the value of Rm/M lies from 70 to 80, and the value of Kt/M lies from 500 to 1000. Accordingly, forming a database of healthy persons regarding the values of Rm/M and Kt/M provides estimation indexes of hardness in muscles and tendons with the values of Rm/M (=Zm/M) and Kt/M (=M/Zt).

The estimated Rm/M and Kt/M are very close to the muscle model (see FIG. 9A) called Hill model (Delp S, Loan P, Hoy M, Zajac F E, Fisher S, and Rosen J. An interactive graphics-based model of the lower extremity to study orthopaedic surgical procedures. IEFE Trans. on Biomedical Engineering, 37(8), August 1990, 757-767) which is generally used in analysis of walking. As shown in FIG. 9A, the general Hill model includes a contractile element 902 and a parallel elastic part 903 (coils means elasticity) connected in parallel, and a tendon part 901 connected in series with the contactile element 902 and the parallel elastic part 903.

FIG. 9B shows a model which is made by replacing the general parts used in the Hill with these parameters. More specifically, Rm corresponds to: a contactile element (CE) 113; Rt, a contactile element 912; and Kt, a tendon element (series elastic element; SEE) 911. In other words, the tendon element 911 and the contactile element 912 correspond to Zt (see FIG. 7C), and the contactile element 913 corresponds to Zm (see FIG. 7A).

As described above, the muscle model of tapping in the first embodiment is similar to the Hill model, and thus can be considered to be appropriate. However, in the analysis method using the muscle model of tapping according to the first embodiment, there is a difference and un-obviousness from the Hill model in that the estimation index in hardness of muscles used in finger motions is obtained from the speed and the acceleration in the opening and closing periods using the law of inertia.

Experimental Data

With reference to FIGS. 10 to 12, will be described the experimental data in the non-periodical test in the muscle dynamic model of tapping according to the first embodiment. FIGS. 10A and 10B show data in the experiment using as subjects five aged peoples who are healthy without histories of disease such as brain disease (hereinafter referred to as aged peoples). In FIG. 10A, the axis of abscissa represents aged people ID, and the axis of ordinate represents the value of Rm/M where each left bar indicates the value of the left hand and each right bar indicates the value of the right hand. Similarly, in FIG. 10B, the axis of abscissa represents the aged people ID, and the axis of ordinate represents the value of Kt/M.

Figure 11A:
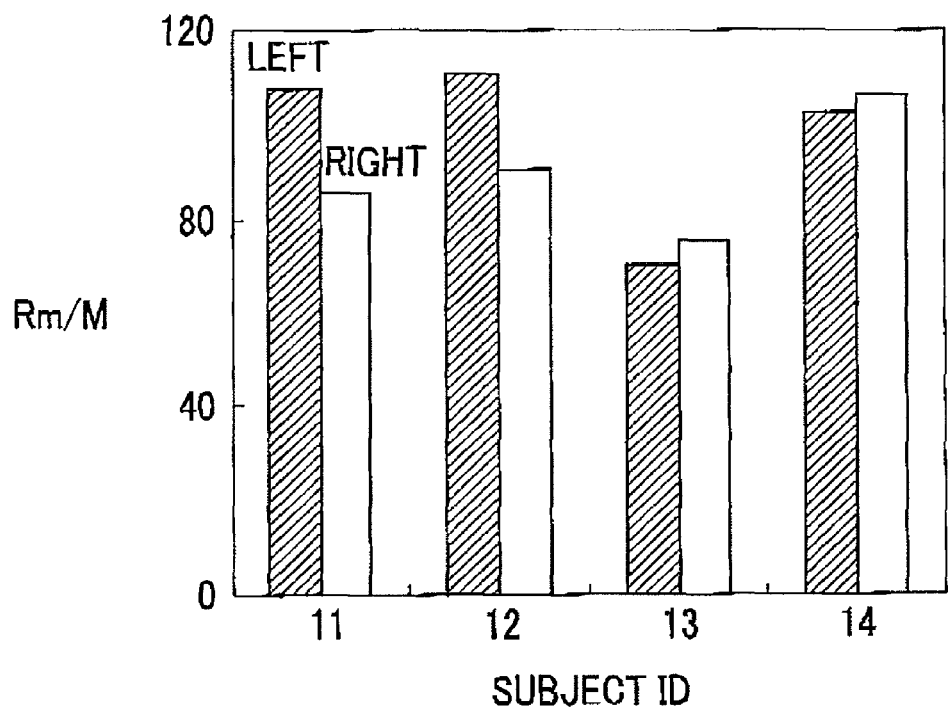
FIGS. 11A and 11B are charts of data of experiment using four Parkinson's disease subjects according to the first embodiment.
Figure 11B:
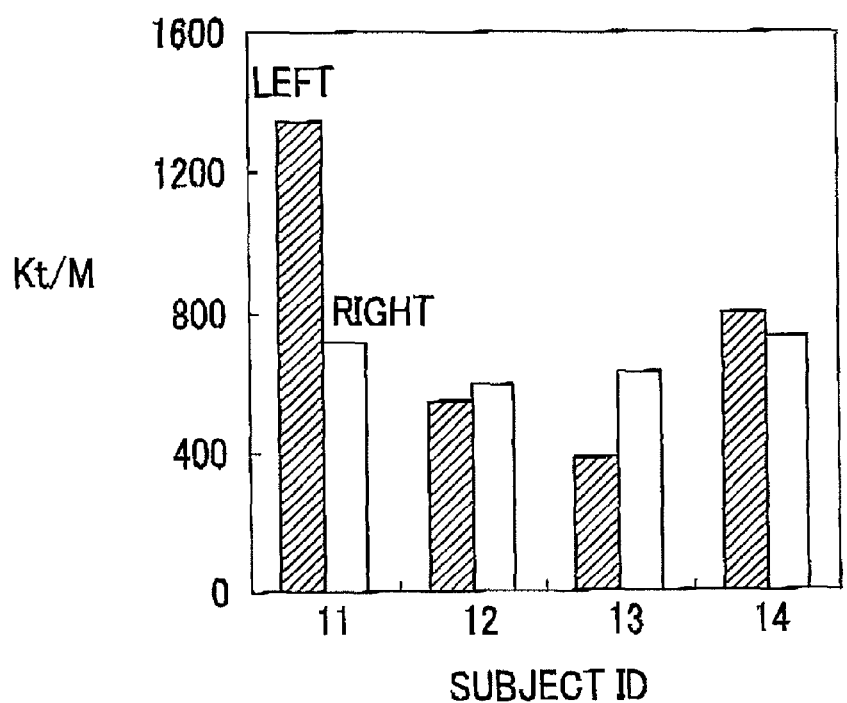

FIGS. 11A and 11B show data of experiment using four Parkinson's disease subjects similarly to the case in FIGS. 10A and 10B. In FIG. 11A, the axis of abscissa represents subject ID, and the axis of ordinate represents the value of Rm/M. In FIG. 11B, the axis of abscissa represents the subject ID, and the axis of ordinate represents the value of Kt/M.

As compared FIGS. 10A and 10B with FIGS. 11A and 11B, there is a tendency that the value of Rm/M and the value of Kt/M in the Parkinson's disease subjects are higher than those in the aged peoples. Therefore, average values of Rm/M and Kt/M are collected from many aged healthy peoples, and values of Rm/M and Kt/M are compared with the average values. The height from the average value can be used as the estimation index for muscles used in finger motion. Here, the normalization by dividing by the mass M of the finger is not essential.

More specifically, a value obtained by normalizing with an equation of Standard Normal Distribution Value=(Measured Value−Average Value)/Standard Deviation) can be used as the estimation index. The "average value" is an average of values measured in healthy aged peoples, and the "standard deviation" is a standard deviation from the values measured in a plurality of healthy aged peoples. Further, the estimation index may be generated with parameter obtained from respective waveforms other than the value of Rm/M and Kt/M.

Using the value of the standard distribution (normalized value) as the estimation index provides a quantitative understanding in how the measured data is deviated from the standard value (average value). More specifically, if the measured value is identical with the average value, the estimation index is 1.0. If the measured value is smaller than the average value, the estimation index becomes a value smaller than the standard value, for example, 0.8. If the measured value is greater than the average value, the estimation index becomes a value greater than the standard value, for example, 1.3. These values of the estimation index are displayed on the display 124 of the living body inspection apparatus 108 to give the operator and the subject an estimation base the estimation index.

Figure 12A:
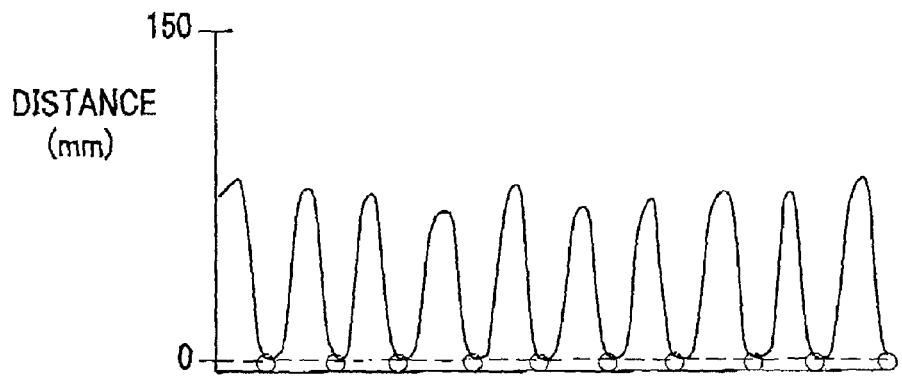
FIGS. 12A to 12D are charts of waveforms used in process of calculating the values of Rm/M and Kt/M for each tapping according to the first embodiment.
Figure 12B:
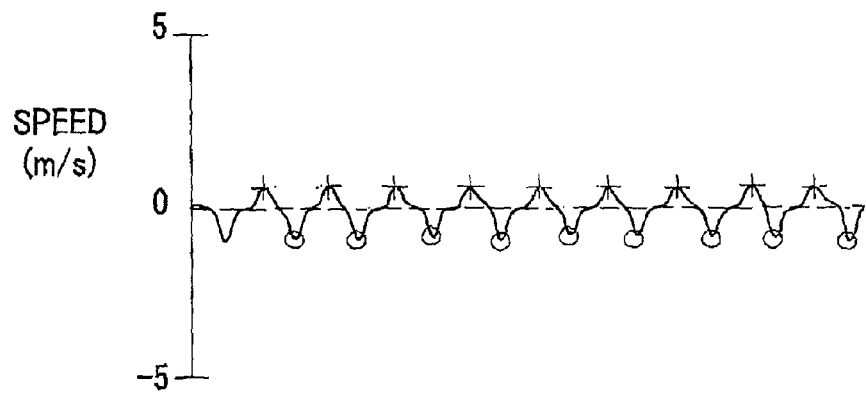
Figure 12C:
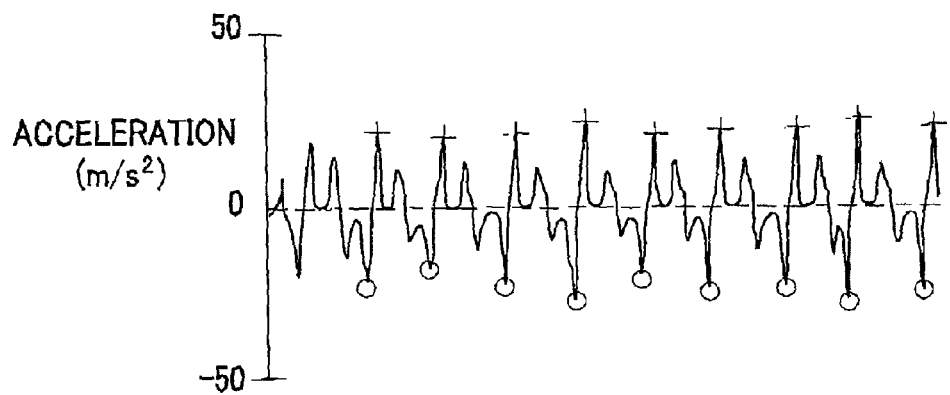
Figure 12D:
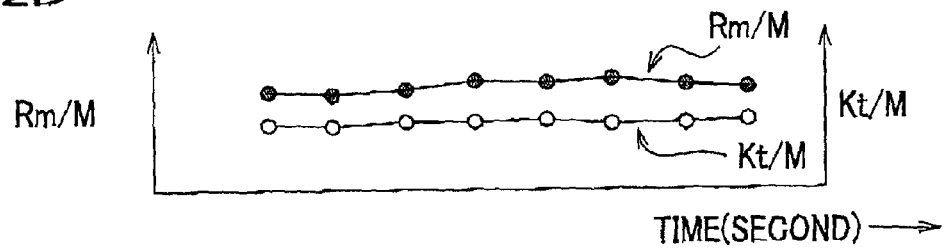

Further, the values of Rm/M and the values of Kt/M may be calculated for each tapping and displayed. FIGS. 12A to 12D are charts for illustrating the process of calculating the values of Rm/M and Kt/M for each tapping. FIGS. 12A to 12C are similar to FIGS. 3A to 3C, and a duplicated description will be omitted. As shown in FIG. 12D, the value of Rm/M and the value of Kt/M can be calculated and displayed. As mentioned above, the estimation index in hardness of the muscles used for finger motion can be calculated and used on the basis of difference between the healthy people and the Parkinson's disease subjects. For example, the values of Rm/M and Kt/M of the healthy people do not largely vary even after twenty second passes. On the other hand, the values of Rm/M and Kt/M of Parkinson's disease subjects largely vary after twenty seconds passes.

As mentioned above, the living body inspection system S of the first embodiment provides the estimation index in hardness of the muscles or the like used in the finger motion through dynamically analyzing the finger motion of the subject. In other words, for example, in the case of the Parkinson's disease subject, it is frequent that muscles in the whole body or a part of muscles are always powered. This may harden the muscles. However, the analysis on the basis of the muscle dynamic model according to the first embodiment provides an adequate estimation index in hardness of the muscles.

The present invention is not limited to the first embodiment, but may be modified.

For example, the present invention is effectively applicable to examination of degenerative affection such as rheumatic and other cranial nerve disease such as brain infarct in addition to the examination of Parkinson's disease.

Further, the structure of the hardware and programs can be modified without departure from the spirit of the present invention.

Second Embodiment

Will be described a second embodiment of the present invention.

The difference from the first embodiment is as follows:

The motion of the finger in a nearly open status (a status near the status where two fingers are fully opened) and the motion of the finger in a nearly contact status (a status near the status where two fingers are closed or contact) are separately processed to provide more precise model or calculation of the motion of two finger.

A general structure of the living body inspection apparatus according to the second embodiment is the same as that of the first embodiment as shown in FIGS. 1 and 2, and thus a duplicated description is omitted.

Figure 13A:
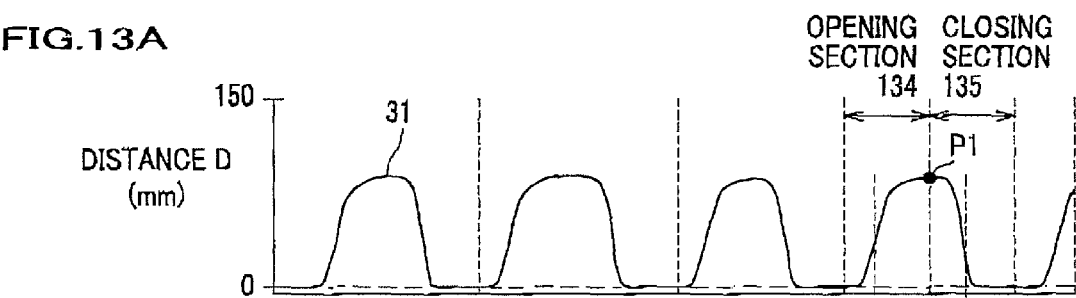
FIGS. 13A to 13C are charts for showing an example of data obtained by tapping of a subject according to a second embodiment of the present invention.
Figure 13B:
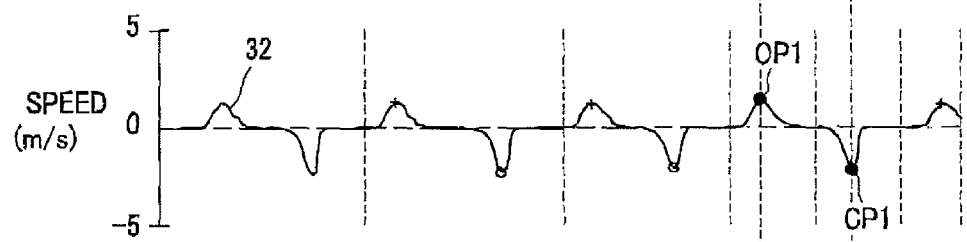
Figure 13C:
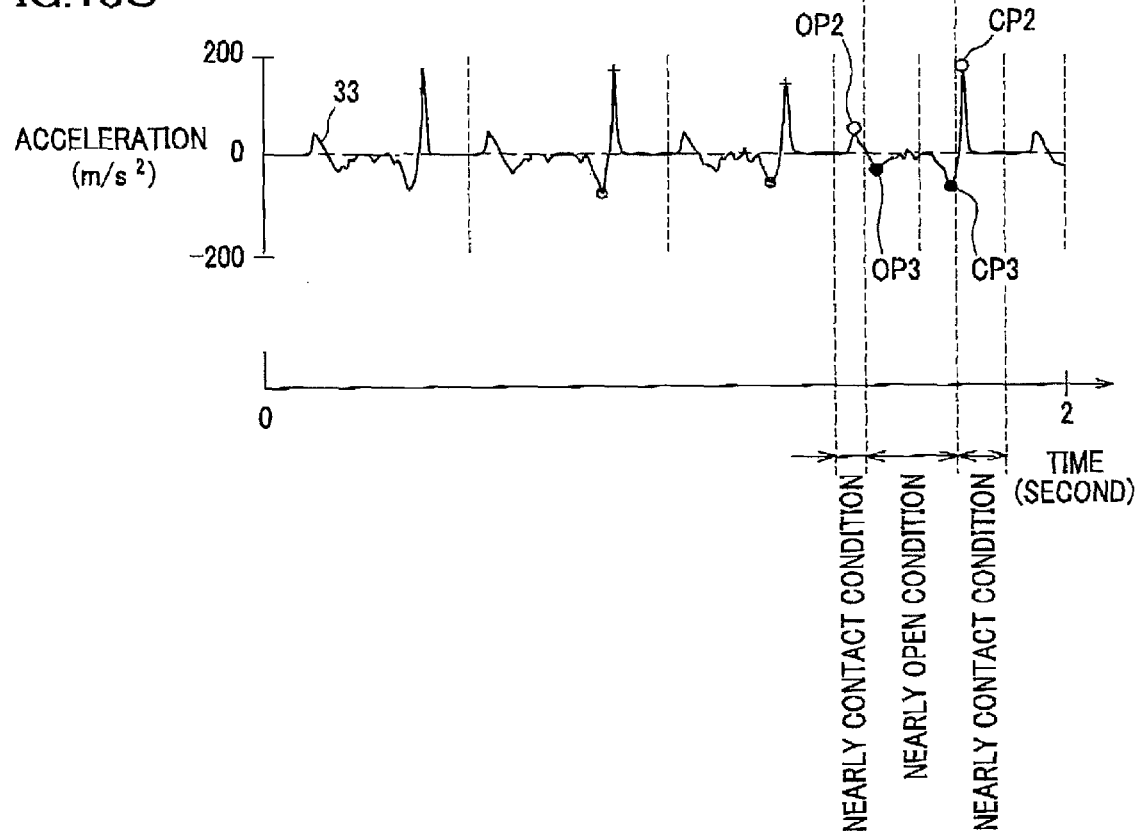

FIGS. 13A to 13C show an example of data obtained through tapping of a subject (opening and closing motion of two fingers (thumb T and one of the other fingers). FIGS. 13A to 13C are charts showing parts of the waveforms in FIGS. 3A to 3C, expanded in the time base, and thus, common explanation will be omitted.

As shown in FIGS. 13A to 13C, each cycle of tapping is divided into the opening section 134 and the closing section 135. A boundary between the opening section 134 and the closing section 135 in FIG. 13A is a point P1 where the distance D (mm) between two fingers has a maximum value. In period of the opening section 134, the subject conducts opening motion of two fingers and conducts closing motion of two fingers in the closing section 135.

In FIG. 13B, a point OP1 is a positive peak (local maximum value) of speed of two fingers being opening, and a point CP1 is a negative peak (local maximum value) of speed of two fingers being closing.

In FIG. 13C, a point OP2 is a positive peak (local maximum value) of acceleration of two fingers being opening, and a point OP3 is a negative peak (local maximum value) of acceleration of two fingers being opening.

In FIG. 13C, a point CP2 is a positive peak (local maximum value) of acceleration of two fingers being closing, and a point CP3 is a negative peak (local maximum value) of acceleration of two fingers being closing.

Here, in the period including the opening section 134 and the closing section 135, for example, a period from the point OP1 to the point CP1 is that including a motion in the nearly open condition of two fingers and the other period is that including a motion in the nearly contact condition of two fingers. In the second embodiment, for each period, values of Vo, Ao, Vc, and Ac are calculated and used. Here, as the values of Vo, Ao, Vc, and Ac in the nearly open condition of open of two fingers, the values at the points OPT, OP3, CP1, and CP3 are used (see Table 1). Further, as the values of Vo, Ao, Vc, and Ac in the nearly contact condition of two fingers, the values at the points OP1, OF2, CP1, and CF2 are used (see Table 1). In the second embodiment, Vo represents an average local maximum speed in the opening period, Ao represents an average local maximum acceleration in the opening period, Vc represents an average local maximum speed in the closing period, and Ac represents an average local maximum acceleration in the closing period also.

TABLE 1

| Nearly Open Condition | Nearly Contact Condition |
|---|---|
| Value of OP1 is used for Vo | Value of OP1 is used for Vo |
| Value of OP3 is used for Ao | Value of OP2 is used for Ao |
| Value of CP1 is used for Vc | Value of CP1 is used for Vc |
| Value of CP3 is used for Ac | Value of CP2 is used for Ac |

Will be described a Kinematic analysis model according to the second embodiment. The same explanation as that in the first embodiment will be omitted. Eqs. (1), (2), and (3) are also used and the concept in introducing Eqs. (1), (2), and (3) is the same as that in the first embodiment.

Similar to the first embodiment, to estimate the value of A/V, the local maximum speeds, the local maximum acceleration in the opening period and those in the closing period are extracted for all tapping cycles as shown in FIGS. 13B and 13C.

Figure 14A:
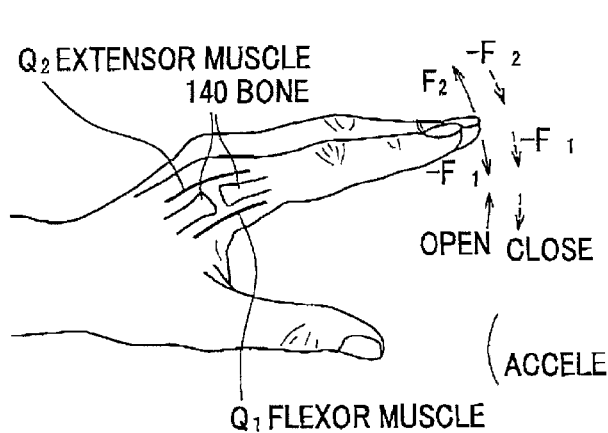
FIG. 14A is an illustration of the hand of the subject in a nearly open condition of fingers according to the second embodiment.
Figure 14B:
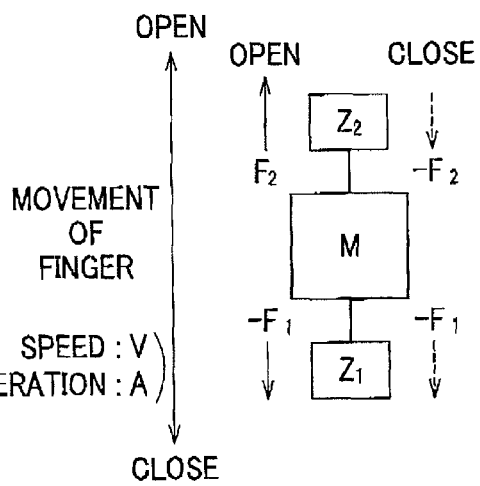
FIG. 14B is a status of an equivalent circuit of the model shown in FIG. 14A according to the second embodiment.

FIGS. 14A to 14D are illustrations of describing the Kinematic analysis model according to the second embodiment. FIG. 14A illustrates a nearly open condition of fingers of the subject, and FIG. 14B is a status of an equivalent circuit of the dynamic model shown in FIG. 14A.

During tapping, actually, both the thumb T and the index finger F move. However, to simplify the explanation, it is assumed that the thumb T is fixed and only the index finger F moves as shown in FIG. 14A. Further for simply modeling the structure of the actual hand of the subject, it is assumed that the index finger F includes a bone 140, a flexor muscle $Q_1$ and an extensor muscle $Q_2$ therein.

The flexor muscle $Q_1$ serves as a role for approaching the index finger F to the thumb T by contraction in response to a subject's intention. The extensor muscle $Q_2$ serves as a role for separating the index finger F from the thumb T by contraction in response to a subject's intention.

$F_1$ indicates a resultant force of a force generated by the flexor muscle $Q_1$ and a spring force by a tendon connected to the flexor muscle $Q_1$ (hereinafter referred to as "a force on the side of the flexor muscle $Q_1$"). $P_2$ indicates a resultant force of a force generated by the extensor muscle $Q_2$ and a spring force by a tendon connected to the extensor muscle $Q_2$ (hereinafter referred to as "a force on the side of the extensor muscle $Q_2$"). Further, it is assumed that $F_1$ and $F_2$ have values equal to zero or more, and an opening direction of two fingers is positive direction.

Here, from a fact that in the nearly open condition, when the subject weakens power, two fingers naturally become close to each other, it is assumed that when two fingers are being opened, a reaction force by the tendon of the flexor muscle $Q_1$ is generated in addition to a contracting force of the extensor muscle $Q_2$. Further, it is assumed that when two fingers are being closed, a pressing force (supporting force) by the tendon of the extensor muscle $Q_2$ is generated in addition to a contracting force by the flexor muscle $Q_1$.

In other word, as shown in FIG. 14B, if two fingers are being opened in the nearly open condition, a force $F_2$ on the side of the extensor muscle $Q_2$ serves as a drive force which exceeds a force of $-F_1$ on the side of the flexor muscle $Q_1$ to open two fingers. In this case, as an equation of motion, Eq. (13a) is given. Modification of this equation with Eq. (1) provides Eq. (13b). Further modification of Eq. (13b) provides Eq. (13c).

$$-F_1 + F_2 = MA_o \tag{13a}$$

$$(-Z_1 + Z_2)V_o = MA_o \tag{13b}$$

$$\frac{(-Z_1 + Z_2)}{M} = \frac{A_o}{V_o} \tag{13c}$$

As shown in FIG. 14B, when two fingers is being closed in the nearly open condition, the force of $-F_1$ on the side of the flexor muscle $Q_1$ serves as a drive force to close two fingers in addition to the force of $-F_2$ on the side of the extensor muscle $Q_2$. In this case, as an equation of motion, Eq. (14a) is given. Modification of this equation with Eq. (1) provides Eq. (14b). Further modification of Eq. (14b) provides Eq. (14c).

$$-F_1 - F_2 = -MA_c \tag{14a}$$

$$(-Z_1 - Z_2)V_c = -MA_c \tag{14b}$$

$$\frac{(Z_1 + Z_2)}{M} = \frac{A_c}{V_c} \tag{14c}$$

Solving simultaneously equations of Eqs. (13c) and (14c) provides the following Eq. (15) (calculation equation for opening motion in the nearly open condition), and Eq. (16) (calculation equation for closing motion in the nearly open condition).

$$\frac{Z_1}{M} = \left(\frac{A_c}{V_c} - \frac{A_o}{V_o}\right)\Big/2 \tag{15}$$

$$\frac{Z_2}{M} = \left(\frac{A_c}{V_c} + \frac{A_o}{V_o}\right)\Big/2 \tag{16}$$

Using Eqs. (15) and (16) provides (estimates) values of $Z_1/M$ and $Z_2/M$ from the values of Ao, Ac, and Vo in the nearly open condition. In this case, $Z_1/M$ represents a mechanical impedance regarding the closing motion of two fingers, and $Z_2/M$ represents a mechanical impedance regarding the opening motion of two fingers.

Figure 14C:
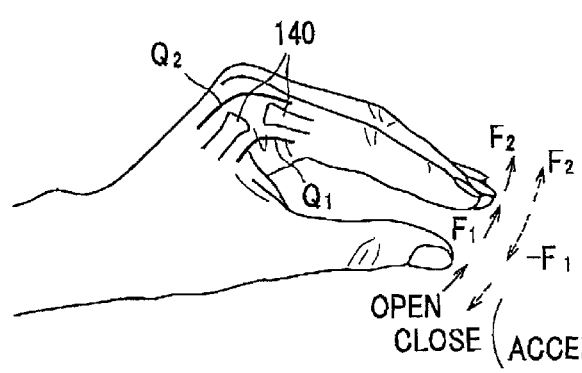
FIG. 14C is an illustration of the hand of the subject in a nearly contact condition of fingers according to the second embodiment.

On the other hand, in the nearly contact condition in FIG. 14C, from the fact that two fingers are naturally separated when the subject weakens power, it is assumed that when two fingers are being opened, a supporting force by the tendon of the flexor muscle $Q_1$ is generated in addition to a contracting force by the extensor muscle $Q_2$. Further it is assumed that when two fingers are being closed, a reaction force by the tendon of the extensor muscle $Q_2$ is generated in addition to a contracting force by the flexor muscle $Q_1$.

Figure 14D:
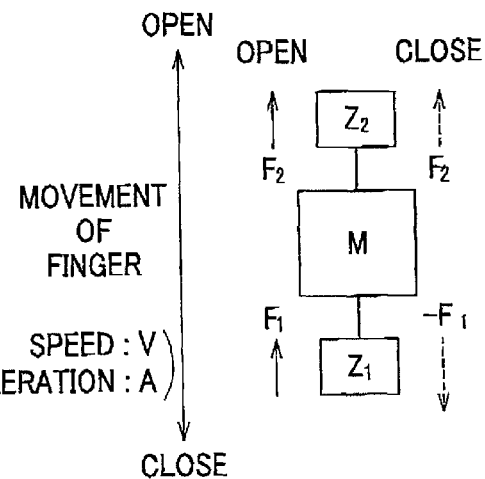
FIG. 14D is a status of an equivalent circuit of the model shown in FIG. 14C according to the second embodiment of the present invention.

In other words, as shown in FIG. 14D, when two fingers are being opened in the nearly contact condition, a force $F_2$ on the side of the extensor muscle $Q_2$ serves as a drive force in addition to the force $F_1$ on the side of the flexor muscle $Q_1$ to open two fingers, In this case, as an equation of motion, Eq. (17a) is given. Modification of Eq. (17a) with Eq. (1) provides Eq. (17b). Further modification of Eq. (17b) provides Eq. (17c).

$$F_1 + F_2 = MA_o \tag{17a}$$

$$(Z_1 + Z_2)V_o = MA_o \tag{17b}$$

$$\frac{(Z_1 + Z_2)}{M} = \frac{A_o}{V_o} \tag{17c}$$

Further, as shown in FIG. 14D, when two fingers are being closed in the nearly contact condition, the force $-F_1$ on the side of the flexor muscle $Q_1$ exceeds the force $F_2$ on the side of the extensor muscle $Q_2$ to close the fingers. In this case, as an equation of motion, Eq. (18a) is given. Modification of Eq. (18a) with Eq. (1) provides Eq. (18b). Further modification of Eq. (18b) provides Eq. (18c).

$$-F_1 + F_2 = -MA_c \tag{18a}$$

$$(-Z_1 + Z_2)V_c = -MA_c \tag{18b}$$

$$\frac{(Z_1 - Z_2)}{M} = \frac{A_c}{V_c} \tag{18c}$$

Solving simultaneously equations of Eqs. (17c) and (18c) provides the following Eq. (19) (calculation equation for opening motion in the nearly contact condition), and Eq. (20) (calculation equation for closing motion in the nearly contact condition).

$$\frac{Z_1}{M} = \left(\frac{A_o}{V_o} + \frac{A_c}{V_c}\right)\Big/2 \tag{19}$$

$$\frac{Z_2}{M} = \left(\frac{A_o}{V_o} - \frac{A_c}{V_c}\right)\Big/2 \tag{20}$$

Using Eqs. (19) and (20) provides (estimates) value of $Z_1/M$ and $Z_2/M$ from the values of Ao, Ac, Vo, and Vc in the nearly contact condition.

FIGS. 15A to 15D show analysis results of finger motions measured by the periodic test regarding motion of two fingers in the nearly open condition (a condition near the condition that two fingers are opened). FIG. 15A shows an analysis result of woman's left hand, including curves 1001 to 1004. FIG. 15B shows an analysis result of woman's right hand, including curves 1011 to 1014. FIG. 15C shows an analysis result of man's left hand, including curves 1021 to 1024. FIG. 15D shows an analysis result of man's right hand, including curves 1031 to 1034. In addition, a length of an upward bar and a downward bar extending from each of points (the close circle, open circle, close triangle, and open triangle) represents a standard deviation. This shows that almost all values have small standard deviations. In other words, these values have low deviations. This fact shows that the values are reliable data.

As shown in FIG. 15A, the curve 1001 shows the values of A/V in the opening period. The curve 1002 shows the values of [(C+O)/2] ($Z_2$) which is obtained by adding the value of A/V in the closing periods and the value of A/V in the opening periods, which result is divided by "2". The curve 1003 shows the values of [(C−O)/2]($Z_1$) which is obtained by subtracting the value of A/V in the opening periods from the value of A/V in the closing periods, which result is divided by "2". The curve 1004 shows the values of A/V in the closing periods.

Figure 17A:
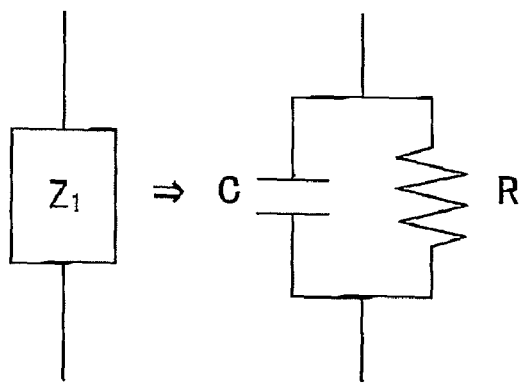
FIGS. 17A to 17D show equivalent circuits according to the second embodiment.
Figure 17B:
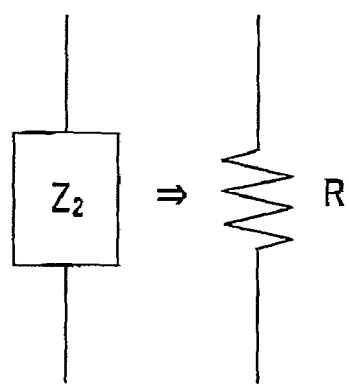

As shown in FIG. 15A, the value of $Z_2$ is a substantially constant value which is not dependent on the frequency. There is a tendency that the value of $Z_1$ decreases with the frequency around 2 to 3 Hz. Accordingly, the mechanical impedances are replaced with equivalent electric circuit elements. Then, as shown in FIG. 17A, $Z_1$ can be considered as a parallel circuit including a resistor R and a capacitor C. The mechanical impedance $Z_2$ can be considered as a resistor R as shown in FIG. 17B. FIGS. 17A to 17D show equivalent circuits similar to FIGS. 7A to 7C.

In FIGS. 15B to 15D, the curves 1011 to 1014, 1021 to 1024, and curves 1031 to 1034 correspond to the curves 1011 to 1014 in FIG. 15A. There are similar tendencies in $Z_1$ and $Z_2$ to the tendency in FIG. 15A. In other words, there is substantially no difference between men and women, and between right and left hands.

FIGS. 16A to 16D show analysis results of finger motions measured by the periodic test regarding motion of two fingers in the nearly contact condition (a condition near the condition that two fingers contact). FIG. 16A shows an analysis result of woman's left hand, including curves 2001 to 2004. FIG. 16B shows an analysis result of woman's right hand, including curves 2011 to 2014. FIG. 16C shows an analysis result of rnan's left hand, including curves 2021 to 2024. FIG. 16D shows an analysis result of man's right hand, including curves 2031 to 2034.

As shown in FIG. 16A, the curve 2001 shows the values of A/V in the opening period. The curve 2002 shows the values of [(O+C)/2] ($Z_1$) which is obtained by adding the value of A/V in the opening period and the value of A/V in the closing periods, which result is divided by "2". The curve 2003 shows the values of [(O−C)/2] ($Z_2$) which is obtained by subtracting the value of A/V in the closing periods from the value of A/V in the opening periods, which result is divided by "2". The curve 2004 shows the values of A/V in the closing periods.

Figure 17C:
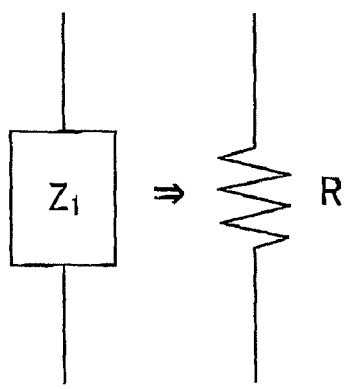
Figure 17D:
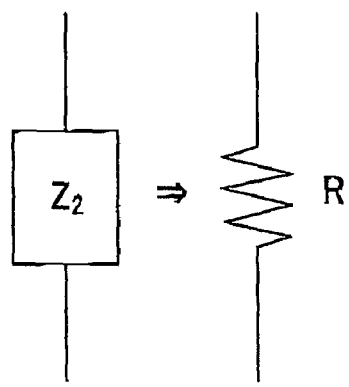

As shown in FIG. 16A, the value of $Z_1$ is a substantially constant value which is not dependent on the frequency. The value of $Z_2$ is a constant value up to a frequency around 3 Hz, and has no value over 4 Hz. Accordingly, as shown in FIGS. 17C and 17D, replacing the mechanical impedances $Z_1$ and $Z_2$ (1 to 3 Hz) with equivalent electric circuit elements provides circuits including a resistor R, respectively.

In FIGS. 16B to 16D, the curves 2011 to 2014, 2021 to 2024, and curves 2031 to 2034 correspond to the curves 2001 to 2004 in FIG. 16A. There are similar tendencies in $Z_1$ and $Z_2$ to the tendency in FIG. 16A. In other words, there is substantially no difference between men and women, and between right and left hands.

With reference to FIGS. 18A to 18C will be described experimental data according to the second embodiment. The subjects are healthy middle aged peoples without brain disease history. FIGS. 18A and 18B shows data regarding motions of two fingers in the nearly open condition, and FIG. 18C shows data regarding motions of two fingers in the nearly contact condition, both of which are measured around 2 Hz.

In FIG. 18A, on the axis of abscissa represents, there are bars of the left and right hands of women, and the left and right hands of men. The axis of ordinate represents values of R/M (white bars correspond to $Z_1$ and the hatched bars correspond to $Z_2$). In the FIG. 18B, the axis of abscissa is similar to that in FIG. 18A, and the axis of ordinate represents the values of K/M (similar to FIG. 10B).

In FIG. 18C, the axis of abscissa is similar to FIG. 18A, and the axis of ordinate corresponds to the values of R/M (white bars correspond to $Z_1$ and the hatched bars correspond to $Z_2$).

Further, in FIGS. 18A and 18C, lines of shapes of "T" on upper side of respective bars represent standard deviations. This shows that most of all values have small standard deviations. In other words, there is small dispersions, which means reliable data.

As shown in FIGS. 18A to 18C, the living body inspection system S according to the second embodiment provides appropriate estimation indexes regarding hardness of muscles used for motion of the fingers of the subject by dynamically analyzing the motion of the fingers of the subject. Further, estimation of respective values regarding the motion of two fingers in the nearly open condition and the nearly contact condition are separately provided. In other words, parameters (respective values) can be given to more accurately comprehend a disease having a tendency that a disorder appears in the nearly contact condition (for example, Parkinson's disease) and for a disease having a tendency that a disorder appears in the nearly open condition (for example, apoplexy).

The second embodiment is not limited to the above description. For example, as similar to the first embodiment, the mechanical impedances can be normalized by divining with the mass of two fingers or normalized with average value and standard deviation, which provides estimation indexes also.

Further the second embodiment can be modified in the hardware and programs and the like without departure from the spirit of the present invention.

As mentioned above, the present invention provides a living body inspection system comprising: a tapping detecting unit for detecting motion data regarding at least one of a distance, a speed, and an acceleration, of two fingers of a hand of a subject, in tapping operation including open and closing motions of the fingers; and a living body inspection apparatus for calculating an estimation index regarding finger motion of the subject on the basis of the motion data, comprising: a storage; and a processing part for conducting at least one of a first process for a nearly open condition of the fingers which is near a condition that the fingers are fully open and a second process for a nearly close condition of the fingers which is near a condition that the fingers are fully closed and storing an estimation index in the storage on the basis of the motion data from the tapping detecting unit.

The first process includes, in the nearly open condition, obtaining (calculating) local maximum values of the speed and the acceleration regarding an opening motion of the fingers in the nearly open condition and obtaining (calculating) local maximum values of the speed and the acceleration regarding a closing motion of the fingers in the nearly open condition; calculating the estimation index regarding the fingers in the nearly open condition with a ratio between the local maximum values of the speed and the acceleration regarding the opening motion in the nearly open condition and a ratio between the local maximum values of the speed and the acceleration regarding the closing motion in the nearly open condition.

The second process includes, in the nearly contact condition, obtaining (calculating) a local maximum value of the speed and the acceleration regarding an opening motion of the fingers in the nearly contact condition and obtaining (calculating) a local maximum value of the speed and the acceleration regarding a closing motion of the fingers in the nearly contact condition; and calculating an estimation index regarding the fingers in the nearly contact condition with a ratio between the local maximum values of the speed and the acceleration regarding the opening motion in the nearly contact condition and a ratio between the local maximum values of the speed and the acceleration regarding the closing motion in the nearly contact condition.

The estimation index is a first mechanical impedance regarding the opening operation of the fingers in the nearly open condition calculated by a first equation of the opening motion in the nearly open condition using a ratio between local maximum values of the speed and acceleration regarding the opening motion in the nearly open condition.

The estimation index is a second mechanical impedance regarding the closing operation of the fingers in the nearly open condition calculated and by a second equation of the closing motion in the nearly open condition using a ratio between local maximum values of the speed and acceleration regarding the closing motion in the nearly open condition.

The estimation index is a third mechanical impedance regarding the opening operation of the fingers in the nearly contact condition calculated by a third equation of the opening notion in the nearly contact condition using a ratio between local maximum values of the speed and acceleration regarding the opening motion in the nearly contact condition.

The estimation index is a fourth mechanical impedance regarding the closing operation of the fingers in the nearly contact condition calculated and by a fourth equation of the closing motion in the nearly contact condition using a ratio between local maximum values of the speed and acceleration regarding the closing motion in the nearly contact condition.

The processing part divides the first to fourth mechanical impedances by mass of the fingers to convert the first to fourth mechanical impedances to calculate normalized estimation indexes to be stored in the storage. The processing part converts the first and third mechanical impedances regarding the opening motion of the fingers and the second and fourth mechanical impedances regarding the closing motions of the fingers into values normalized with averages and standard deviation of the mechanical impedances, respectively to calculate the estimation index.

According to the present invention, the following is further provided.

The present invention further provides a living body inspection apparatus for calculating an estimation index regarding finger motion of the subject on the basis of motion data obtained from a tapping detecting unit for detecting the motion data regarding at least one of a distance, a speed, and an acceleration, of two fingers of a hand of a subject, in open and closing motion of the fingers, comprising a storage; and a processing part for conducting at least one of a first process for a nearly open condition of the fingers which is near the condition that the fingers are fully open and a second process for a nearly close condition of the fingers which is near the condition that the fingers are fully closed and storing an estimation index in the storage on the basis of the motion data from the tapping detecting unit. The first process includes, in the nearly open condition, obtaining (calculating) local maximum values of the speed and the acceleration regarding an opening motion of the fingers in the nearly open condition and obtaining (calculating) local maximum values of the speed and the acceleration regarding a closing motion of the fingers in the nearly open condition; calculating the estimation index regarding the fingers in the nearly open condition with a ratio between the local maximum values of the speed and the acceleration regarding the opening motion in the nearly open condition and a ratio between the local maximum values of the speed and the acceleration regarding the closing motion in the nearly open condition. The second process includes, in the nearly contact condition, obtaining (calculating) a local maximum value of the speed and the acceleration regarding an opening motion of the fingers in the nearly contact condition and obtaining (calculating) a local maximum value of the speed and the acceleration regarding a closing motion of the fingers in the nearly contact condition; and calculating an estimation index regarding the fingers in the nearly contact condition with a ratio between the local maximum values of the speed and the acceleration regarding the opening motion in the nearly contact condition and a ratio between the local maximum values of the speed and the acceleration regarding the closing motion in the nearly contact condition.

The present invention further provides a living body inspection method of calculating an estimation index regarding finger motion of the subject on the basis of motion data obtained from a tapping detecting unit for detecting the motion data regarding at least one of a distance, a speed, and an acceleration, of two fingers of a hand of a subject, in tapping operation including open and closing motions of the fingers with a living body inspection apparatus comprising a storage and a processing part, comprising the steps of: in the processing part, conducting at least one of a first process for a nearly open condition of the fingers which is near the condition that the fingers are fully open and a second process for a nearly close condition of the fingers which is near the condition that the fingers are fully closed and storing an estimation index in the storage on the basis of the motion data from the tapping detecting unit. The first process includes, in the nearly open condition, obtaining (calculating) local maximum values of the speed and the acceleration regarding an opening motion of the fingers in the nearly open condition and obtaining (calculating) local maximum values of the speed and the acceleration regarding a closing motion of the fingers in the nearly open condition; calculating the estimation index regarding the fingers in the nearly open condition with a ratio between the local maximum values of the speed and the acceleration regarding the opening motion in the nearly open condition and a ratio between the local maximum values of the speed and the acceleration regarding the closing motion in the nearly open condition. The second process includes, in the nearly contact condition, obtaining (calculating) a local maximum value of the speed and the acceleration regarding an opening motion of the fingers in the nearly contact condition and obtaining (calculating) a local maximum value of the speed and the acceleration regarding a closing motion of the fingers in the nearly contact condition; and calculating an estimation index regarding the fingers in the nearly contact condition with a ratio between the local maximum values of the speed and the acceleration regarding the opening motion in the nearly contact condition and a ratio between the local maximum values of the speed and the acceleration regarding the closing motion in the nearly contact condition.

The invention claimed is:

1. A living body inspection system comprising:
   a tapping detecting unit that detects motion data regarding at least one of a distance, a speed, and an acceleration, of two fingers of a hand of a subject, in tapping operation including open and closing motions of the fingers; and
   a living body inspection apparatus that calculates an estimation index regarding finger motion of the subject on the basis of the motion data, including:
   a storage; and
   a processing part programmed to:
   obtain a speed and an acceleration on the basis of the motion data from the tapping detecting unit,
   calculate the estimation index by calculating at least one of
   (a) a mechanical impedance regarding the extending force of the fingers, and
   (b) a mechanical impedance regarding an opening and closing force of the fingers, by using the speed and acceleration in a predetermined equation based on a muscle dynamic model, that uses a ratio between the speed and the acceleration, and convert into normalized values the at least one of (a) the mechanical impedance regarding the extending force of the fingers, and (b) the mechanical impedance regarding the opening and closing force of the fingers, by dividing the at least one of the mechanical impedances by a mass of the fingers, and store the normalized values in the storage.

2. The living body inspection system as claimed in claim 1, wherein the processing part converts the mechanical impedance regarding the extending force of the fingers, and the mechanical impedance regarding the opening and closing force of the fingers, into values normalized with average values and standard deviations as the calculated estimation index.

3. The living body inspection system as claimed in claim 1, wherein the processing part calculates the mechanical impedance regarding the extending force of the fingers as a mechanical resistance, and calculates the opening and closing force of the fingers as a compliance or a spring constant.

4. The living body inspection system as claimed in claim 1, wherein the predetermined equation comprises:

an equation that calculates a value obtained by adding a value of the speed divided by the acceleration regarding an opening motion of the fingers to a value of the speed divided by the acceleration regarding an closing motion of the fingers; and an equation that calculates a value obtained by subtracting a value of the speed divided by the acceleration regarding a closing motion of the fingers from a value of the speed divided by the acceleration regarding an opening motion of the fingers.

5. The living body inspection system as claimed in claim 1, wherein the processing part is programmed by, and configured by, instructions stored in the storage.

6. A living body inspection apparatus that calculates an estimation index regarding finger motion of the subject on the basis of motion data obtained from a tapping detecting unit that detects the motion data regarding at least one of a distance, a speed, and an acceleration, of two fingers of a hand of a subject, in open and closing motion of the fingers, comprising:

a storage; and a processing part programmed to:

obtain a speed and an acceleration on the basis of the motion data from the tapping detecting unit, calculate the estimation index by calculating at least one of (a) a mechanical impedance regarding the extending force of the fingers, and (b) a mechanical impedance regarding an opening and closing force of the fingers, by using the speed and acceleration in a predetermined equation based on a muscle dynamic model, that uses a ratio between the speed and the acceleration, and convert into normalized values the at least one of (a) the mechanical impedance regarding the extending force of the fingers, and (b) the mechanical impedance regarding the opening and closing force of the fingers, by dividing the at least one of the mechanical impedances by a mass of the fingers, and store the normalized values in the storage.

7. The living body inspection apparatus as claimed in claim 6, wherein the processing part converts the mechanical impedance regarding the extending force of the fingers, and the mechanical impedance regarding the opening and closing force of the fingers, into values normalized with average values and standard deviations as the calculated estimation index.

8. The living body inspection apparatus as claimed in claim 6, wherein the processing part calculates the mechanical impedance regarding the extending force of the fingers as a mechanical resistance, and calculates the opening and closing force of the fingers as a compliance or a spring constant.

9. The living body inspection apparatus as claimed in claim 6, wherein the predetermined equation comprises:

an equation that calculates a value obtained by adding a value of the speed divided by the acceleration regarding an opening motion of the fingers to a value of the speed divided by the acceleration regarding an closing motion of the fingers; and an equation that calculates a value obtained by subtracting a value of the speed divided by the acceleration regarding a closing motion of the fingers from a value of the speed divided by the acceleration regarding an opening motion of the fingers.

10. The living body inspection apparatus as claimed in claim 6, wherein the processing part is programmed by, and configured by, instructions stored in the storage.

11. A living body inspection method of calculating an estimation index regarding finger motion of the subject on the basis of motion data obtained from a tapping detecting unit that detects the motion data regarding at least one of a distance, a speed, and an acceleration, of two fingers of a hand of a subject, in open and closing motion of the fingers, by using a living body inspection apparatus comprising a storage and a processing part, wherein the processing part is configured by instructions stored in the storage, comprising the steps of:

obtaining the speed and the acceleration on the basis of the motion data from the tapping detecting unit; and calculating the estimation index by calculating at least one of (a) a mechanical impedance regarding the extending force of the fingers, and (b) a mechanical impedance regarding an opening and closing force of the fingers, by using the speed and acceleration in a predetermined equation based on a muscle dynamic model, that uses a ratio between the speed and the acceleration, and converting into normalized values the at least one of (a) the mechanical impedance regarding the extending force of the fingers, and (b) the mechanical impedance regarding the opening and closing force of the fingers, by dividing the at least one of the mechanical impedances by a mass of the fingers, and storing the normalized values in the storage.

12. The living body inspection method as claimed in claim 11, wherein the processing part converts the mechanical impedance regarding the extending force of the fingers, and the mechanical impedance regarding the opening and closing force of the fingers, into values normalized with average values and standard deviations as the calculated estimation index.

13. The living body inspection method as claimed in claim 11, wherein the processing part calculates the mechanical impedance regarding the extending force of the fingers as a mechanical resistance, and calculates the opening and closing force of the fingers as a compliance or a spring constant.

14. The living body inspection method as claimed in claim 11, wherein the predetermined equation comprises:

an equation that calculates a value obtained by adding a value of the speed divided by the acceleration regarding an opening motion of the fingers to a value of the speed divided by the acceleration regarding an closing motion of the fingers; and an equation that calculates a value obtained by subtracting a value of the speed divided by the acceleration regarding a closing motion of the fingers from a value of the speed divided by the acceleration regarding an opening motion of the fingers.

* * * * *